(12) United States Patent
Yaakov et al.

(10) Patent No.: US 9,657,260 B2
(45) Date of Patent: May 23, 2017

(54) METHOD AND SYSTEM FOR CONTINOUS MONITORING OF TOXICITY

(71) Applicants: Yissum Research Development Company of The Hebrew University of Jerusalem, Ltd., Jerusalem (IL); Fraunhofer-Gesellschaft zur Förderung der angewandten Forschung e.V., Munich (DE); Colibri Photonics GmbH, Potsdam (DE)

(72) Inventors: Nahmias Yaakov, Rishon le Zion (IL); Sebastian Prill, Berlin (DE); Magnus Jaeger, Berlin (DE); Danny Bavli, Jerusalem (IL); Elmar Schmälzlin, Potsdam (DE)

(73) Assignees: Yissum Research Development Company of the Hebrew University of Jerusalem, Ltd., Jerusalem (IL); Colibri Photonics GmbH, Potsdam (DE); Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 0 days.

(21) Appl. No.: 14/666,656

(22) Filed: Mar. 24, 2015

(65) Prior Publication Data

US 2015/0268224 A1 Sep. 24, 2015

Related U.S. Application Data

(60) Provisional application No. 61/969,377, filed on Mar. 24, 2014.

(51) Int. Cl.
| | | |
|---|---|---|
| *G01N 33/50* | (2006.01) |
| *C12M 1/32* | (2006.01) |
| *C12M 1/00* | (2006.01) |
| *C12M 3/06* | (2006.01) |
| *C12M 1/42* | (2006.01) |
| *C12M 1/34* | (2006.01) |
| *C12M 1/12* | (2006.01) |
| *B01L 3/00* | (2006.01) |

(52) U.S. Cl.
CPC ............ *C12M 23/12* (2013.01); *C12M 23/16* (2013.01); *C12M 23/28* (2013.01); *C12M 29/10* (2013.01); *C12M 35/04* (2013.01); *C12M 41/32* (2013.01); *C12M 41/46* (2013.01); *G01N 33/5008* (2013.01); *G01N 33/5014* (2013.01); *B01L 3/5085* (2013.01); *B01L 2300/0636* (2013.01); *B01L 2300/0663* (2013.01); *B01L 2300/0829* (2013.01); *C12M 25/14* (2013.01); *C12M 25/16* (2013.01)

(58) Field of Classification Search
CPC .................................................... C12M 23/28
See application file for complete search history.

(56) References Cited

FOREIGN PATENT DOCUMENTS

| EP | 1510817 | 3/2005 |
| EP | 1820846 | 8/2007 |
| WO | 9947922 | 9/1999 |
| WO | 0126609 | 4/2001 |
| WO | 2007084655 | 7/2007 |

OTHER PUBLICATIONS

Grist et al. Sensor, 2010, 10:9286-9316.*
Search Report from corresponding European application No. 15160661.3.

* cited by examiner

*Primary Examiner* — Bin Shen
(74) *Attorney, Agent, or Firm* — Roach Brown McCarthy & Gruber, P.C.; Kevin D. McCarthy

(57) ABSTRACT

Systems, kits and methods for non-invasive, long-term, real-time monitoring of one or more physiological parameters of a cell, including but not limited to oxygen uptake, are provided.

18 Claims, 20 Drawing Sheets

METHOD AND SYSTEM FOR CONTINOUS MONITORING OF TOXICITY

CROSS-REFERENCE TO RELATED APPLICATIONS

This application claims the benefit of priority of U.S. Provisional Patent Application No. 61/969,377 filed Mar. 24, 2014, the contents of which are incorporated herein by reference in their entirety.

FIELD OF INVENTION

The present invention is directed to; inter alia, a bioreactor system and method for continuous monitoring of toxicity of a molecule of interest.

BACKGROUND OF THE INVENTION

Prescription drugs and cosmetics are used for extensive periods of time, and their development requires demonstration of long-term safety. Major causes of damage include hepatotoxicity, cardiotoxicity, and neurotoxicity, and nephrotoxicity. Current methods to detect toxicity rely on large number of cells, and dozens of end-point fluorescent, colorimetric, or histological assays dramatically increasing the cost of toxicity screening. Inherently, these techniques provide limited toxicokinetics information. While this is a marginal concern for evaluation of acute toxicity, toxicokinetic information is critical for safety evaluation of prescription drugs and cosmetics. Such a repeated-dose response assay requires two months of daily administration to demonstrate chemical safety of chronic exposure for up to one year. Until now, only animal models could serve these requirements, as it is difficult to maintain cells in culture for over 28 days. However, animal model are inaccurate with 70% of the compounds found toxic in animals are not toxic in humans, and vice versa.

Microfluidic liver-on-chip devices offer an alternative to animal experiments as they can mimic the native microenvironment and support long-term function under continuous perfusion. One critical advantage of microfluidics is the ability to expose cells to a stable stimulation over time, eliminating the rapid loss of signal due to non-specific adsorption and metabolism that characterizes both static in vitro assays and in vivo. Stable microfluidic stimulation permits the acquisition of reliable information about the effect of a specific dose, rather than the response of cells to a rapidly changing drug concentration. Regrettably, current devices still rely on end-point histological or molecular analysis of function to assess the toxicological effect of a molecule of interest, e.g., a drug. It is clear that real-time measurement of cell viability is needed.

Oxygen uptake is a critical measurement of mitochondrial function and metabolic activity (Green and Reed 1998; Han et al. 2013). There is a need for reliably measuring oxygen on the microscale. Regretfully, measurements of fluorescence intensity, such as by particles whose fluorescence is quenched in the presence of oxygen, are affected by small changes in focus, particle migration, and cell movement making these types of probes unreliable for real time measurements.

One of the main intracellular targets of drug-induced liver injury is mitochondrial function, either through direct damage to the respiratory complex (e.g. NAPQI) or though secondary mechanisms such as ER stress (e.g. tunicamycin). Currently, end-point assays such as MTT or JC1 staining are used to evaluate mitochondrial function or its membrane potential, respectively. An alternative approach will monitor oxygen consumption directly using classical Clark-type electrodes or oxygen-quenchable fluorophores (e.g. ruthenium compounds) (Papkovsky and Dmitriev 2013; Ramamoorthy et al. 2003). However, Clark-type electrodes do not meet the needs of miniature in vitro assays as the electrochemical reaction consumes oxygen during measurement and needs frequent recalibration. On the other hand, optical oxygen sensors are more reliable but have to be physically inserted into the sample or coated on the bottom of the culture chamber. Regretfully, fluorescence intensity measurements are affected by small changes in focus occurring due to movement of the mechanical stage and cells, limiting the utility of optical oxygen sensing (Vanderkooi et al. 1987).

Therefore, there is a need to develop a system for the continuous monitoring of cellular toxicity (e.g., for up to two months) in vitro using human cells. Such a system could mimic human physiology, providing a perfused, three-dimensional microenvironment, in which cellular function is maintained at high levels.

SUMMARY OF THE INVENTION

The present invention provides, in some embodiments, a system, a kit and a method for non-invasive, long-term, real-time monitoring of one or more physiological parameters of a cell, including but not limited to oxygen uptake.

According to one aspect, the invention provides a perfusion bioreactor system comprising:
  a) a disposable chip comprising one or more micro-wells adapted for holding (containing) viable cells;
  b) a connector for connecting the chip to a perfusion element for flowing a perfusion medium in a controlled manner through the chip to provide shear force and nutrient supply; and
  c) one or more oxygen sensing particles adapted for being mixed with said viable cells.

In one embodiment, the diameter of each of the micro-wells is 75 to 3000 micrometers. In another embodiment, the chip comprises a plurality of micro-channels orthogonal to the direction of flow of the perfusion medium. In another embodiment, the chip and/or micro-wells within protect the cells from sheer force of the perfusion medium.

In another embodiment, the cells are or form a three-dimensional structure within the micro-well. In another embodiment, said oxygen sensing particles are mixed with, in contact with or at least partially embedded in said three-dimensional structure of cells.

In another embodiment, the cells are or form a cellular aggregate within the micro-well. In another embodiment, said oxygen-sensing particles are mixed with, in contact with or at least partially embedded in said cellular aggregate.

In another embodiment, the cells form a multi-cell type organoid within the micro-well. In another embodiment, said oxygen sensing particles are mixed with, in contact with or at least partially embedded in said organoid.

In another embodiment, the cells form a spheroid within the micro-well. In another embodiment, said oxygen sensing particles are mixed with, in contact with or at least partially embedded in said spheroid.

In another embodiment, the cells form a tissue or a tissue-like structure within the micro-well. In another embodiment, said oxygen sensing particles are mixed with, in contact with or at least partially embedded in said tissue-like structure.

In another embodiment, the said oxygen sensing particles are fluorescent or phosphorescent particles. In another embodiment, said oxygen sensing particles comprise ruthenium-phenanthroline-based phosphorescence dye. In another embodiment, said oxygen sensing particles are a priori present on the chip. In another embodiment, said oxygen sensing particles are present in a separate container.

In another embodiment, the system further comprises a glucose sensor and/or a lactate sensor. In another embodiment, the system comprises an oxygen sensor, a glucose sensor and a lactate sensor.

In another embodiment, the system has a flow inlet for providing medium and a flow outlet for withdrawing medium. In another embodiment, the glucose and/or the lactate sensor are present in the flow outlet.

In another embodiment, the system further comprises a measuring unit configured to detect and/or measure oxygen, glucose and/or lactate by change of at least one of the following parameters: (a) frequency shift, (b) phase shift, or (c) normalized changed in amplitude.

In another embodiment, the lactate and/or glucose sensors are electrochemically-operated. In another embodiment, the glucose and/or lactate sensor are fluorescent or phosphorescent particles.

In another embodiment, the system comprises live cells present in the disposable chip. In another embodiment, said chip is suitable for marinating viable cells for at least 30 days.

In another embodiment, said cells are selected from the group consisting of: hepatocytes, cardiomyocytes, kidney cells, neurons, enterocytes, or cell lines mimicking their function. In another embodiment, the system comprises two or more types of cells placed in separate micro-wells or mixed together. In another embodiment, the mixed cells are hepatocytes and non-parenchymal cells (e.g., stellate cells, sinusoidal endothelial cells, and kupffer cells). In another embodiment, the parenchymal cell type is mixed with appropriate non-parenchymal cells (e.g., fibroblasts, endothelial cells, and astrocytes).

According to another aspect, the invention provides a method for testing the effect of a substance of interest on one or more physiological parameters of cells the method comprising:
  (i) providing the system of the invention;
  (ii) introducing cells to the micro-well of said system together with said oxygen sensing particles;
  (iii) introducing the substance of interest to the chip; and
  (iv) monitoring changes in oxygen uptake by said cells, thereby testing the effect of a substance of interest on one or more physiological parameters of cells.

In another embodiment, the system comprises a glucose sensor and/or a lactate sensor. In another embodiment, the method further comprises monitoring changes in glucose and/or lactate parameters. In another embodiment, said monitoring oxygen, glucose and/or lactate indicate changes in mitochondrial respiration of the examined cells.

In another embodiment, the substance to be tested is a substance for use in the cosmetic, pharmaceutical, food or agriculture industry.

According to another aspect, the invention provides a kit comprising (i) a disposable chip comprising one or more micro-wells adapted for holding viable cells; and (ii) one or more oxygen sensing particles, and optionally one or more sensors selected from a glucose sensor and/or a lactate sensor.

In one embodiment, said kit comprises the oxygen sensing particles as an integral part of the disposable chip, e.g. are a priori present on the chip. In another embodiment, the oxygen sensing particles present in a separate container of said kit.

In one embodiment, said kit comprises the glucose sensor and/or a lactate sensor as an integral part of the system, e.g. are a priori present on the flow outlet of said system. In another embodiment, the glucose sensor and/or a lactate sensor are present in a separate container of said kit.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DETAILED DESCRIPTION OF THE INVENTION

The present invention provides, in some embodiments, a system and a method for non-invasive, long-term, real-time monitoring of one or more physiological parameters of a cell, including but not limited to mitochondrial respiration.

In one embodiment, the system comprises a perfused microfluidic bioreactor. In some embodiments, the system and method of the present invention comprise microprobes embedded in the examined tissue, particularly lifetime-based luminescence-quenching (LBLQ) microprobes.

As demonstrated hereinbelow, HepG2/C3A cells display increase CYP450 expression following 28 days of perfusion using the system described herein, mimicking in vivo microenvironment (FIG. 2). This functional stabilization permits direct monitoring of oxygen uptake rates using embedded oxygen sensors (e.g., LBLQ microprobes). Advantageously, the system and method described herein eliminate the need for multiple end-point assays, while permitting high throughput, long-term measurements of cell function using small numbers of cells.

Figure 1A:
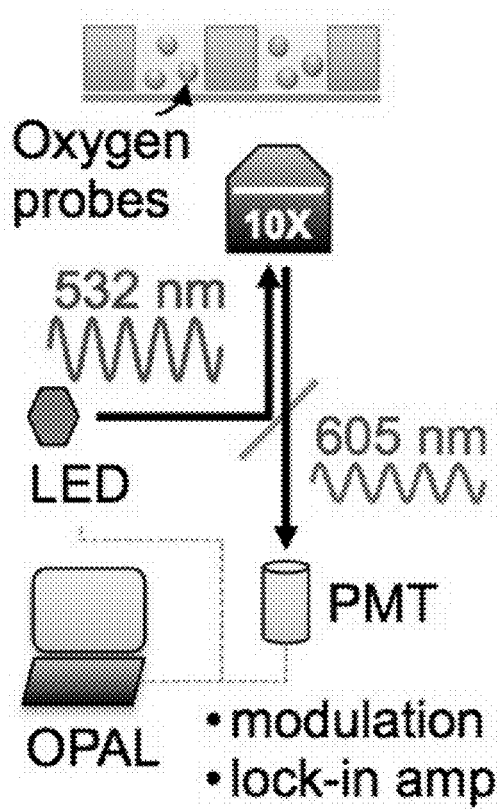
FIGS. 1A-G. A: Scheme of the measurement setup connected to the microscope, comprising an electronic control unit for signal modulation and readsout, a LED for excitation, an optical filter set (531/40, 555, 607/70 nm) and a detector unit containing a photomultiplier (PMT). B: Jablonski diagram describing the generation of phosphorescence with Ru-CPOx beads under the influence of oxygen as its quencher. The quenching of the phosphorescence by ambient triplet oxygen leads to a decrease in signal intensity and phosphorescence decay time (T1) with an increasing concentration of oxygen and vice versa. C: The effect described in B induces a phase shift between the intensitys modulated excitation and emission light. Thus, the degree of phase shift can be used for determining the oxygen concentration. Two superimposed frequencies were used to screen out background interference. D: Fluorescence image of cells and sensor particles after immobilization in a collagen matrix. Blue: DAPI, Orange: Ru-CPOx-Beads. Bar=100 pm. E: Evaluation of the minimum number of simultaneously measured sensor particles that are necessary for obtaining a satisfactory standard error of 1% to 2%. For this, five to ten particles were found to be sufficient. F,G: Fluorescence micrographs and plot describing the independence of the used oxygen measurement system of signal intensity. This was achieved by measuring at the optical focus (highest intensity) and multiple points along the optical axis, successively yielding less signal intensity but an unchanged decay time (i.e. oxygen concentration).
Figure 1B:
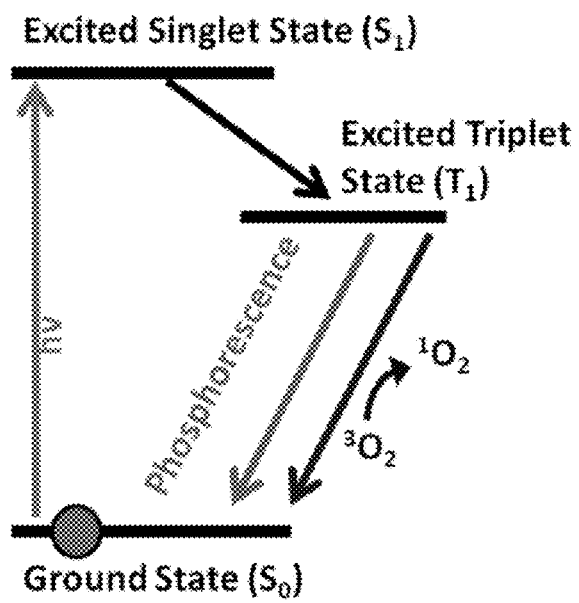
Figure 1C:
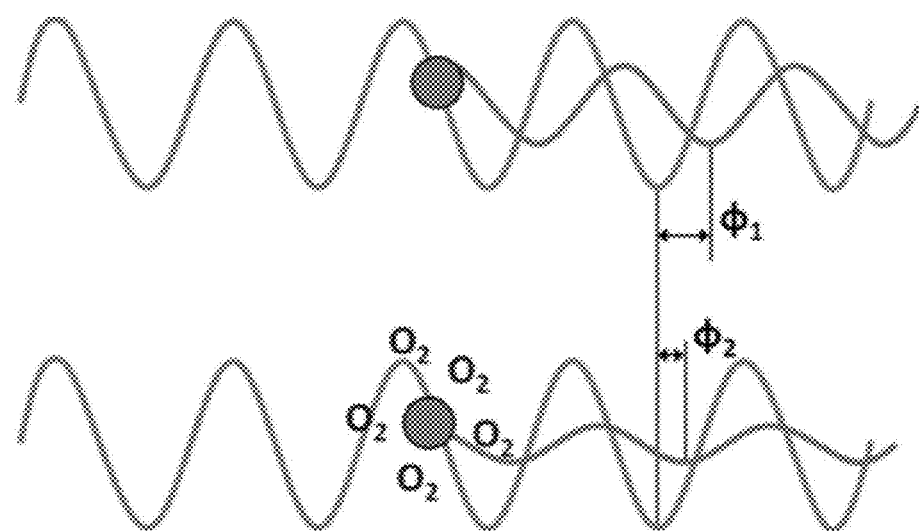
Figure 1D:
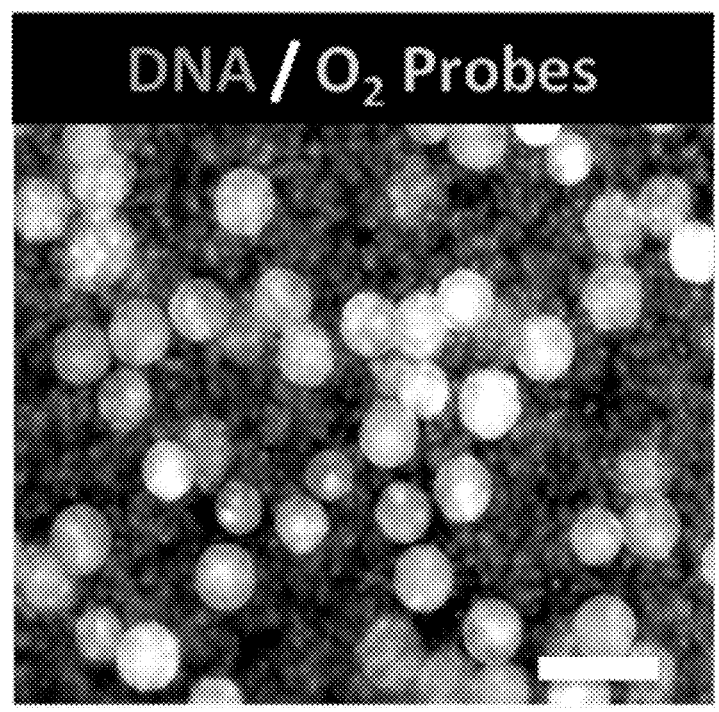
Figure 1E:
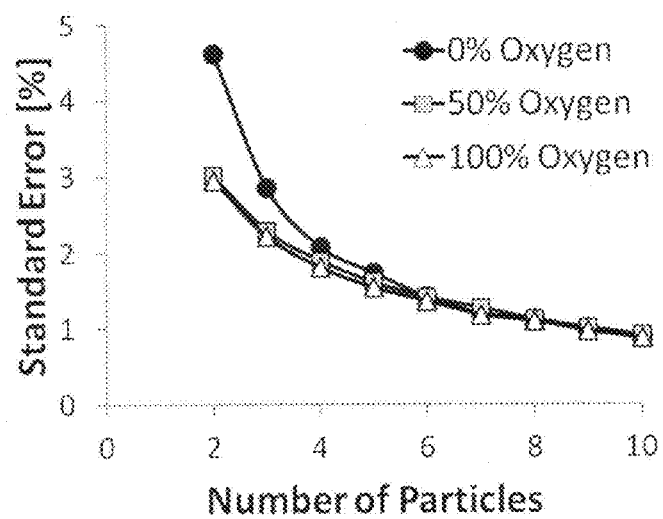
Figure 1F:
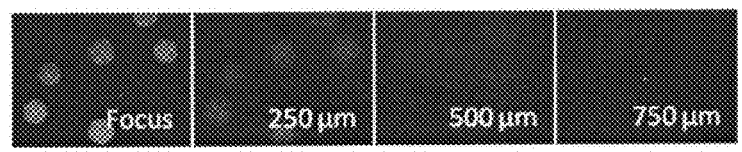
Figure 1G:
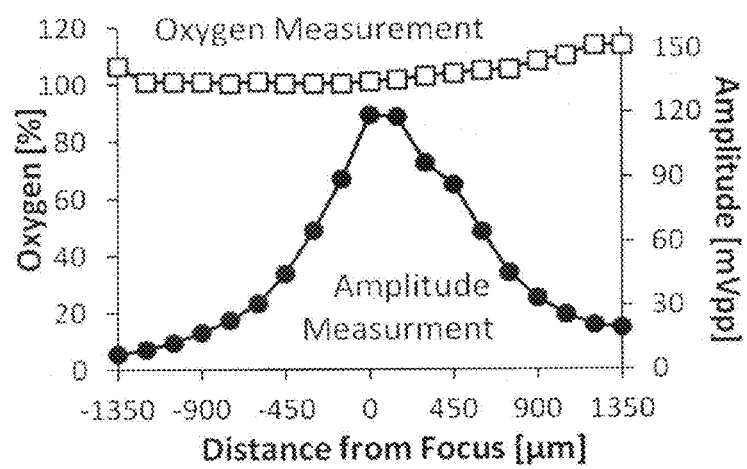
Figure 2A:
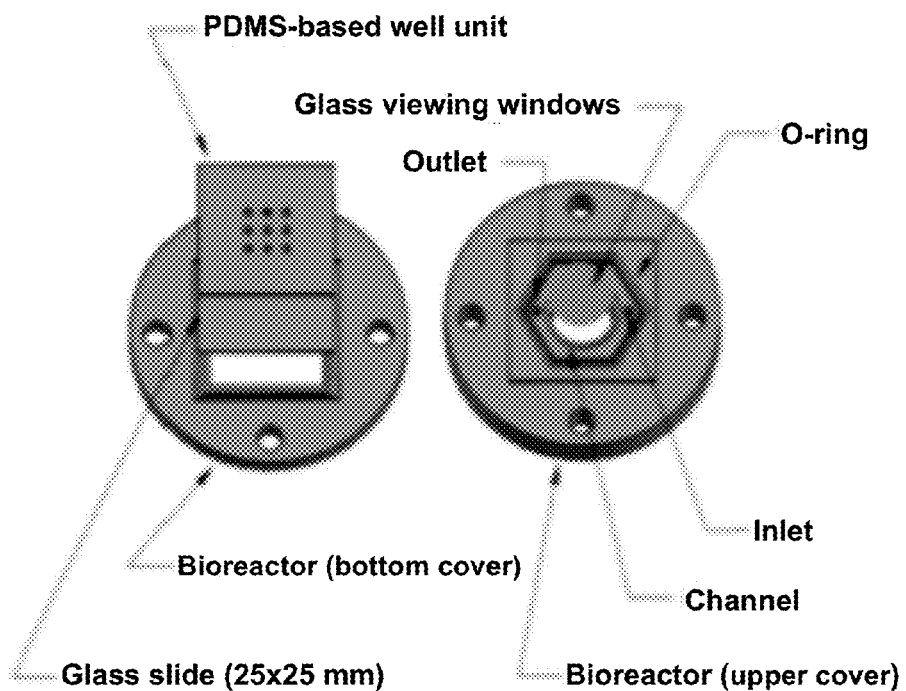
FIGS. 2A-J A: Bioreactor components in overview. Left: bottom part with PDMS microwell insert on glass substrate; top view. Right: top part with glass coverslip for optical accessibility also from top, recess for O-ring and perfusion inlet/outlet; upside down view. B: Longsterm oxygen measurement over 1 month in bioreactor perfused with fresh cell culture medium at 10 pl/min. 100% air represents atmospheric dissolved oxygen concentration (21% $O_2$=210 pmol/L; no consumption) C: Photograph taken during microwell insert seeding procedure. D: Numerical simulation of the shear stress magnitude and (E-F) oxygen concentration along the bioreactor. G: Oxygen concentration variations within the well (from top to bottom), mimicking the in vivo microenvironment. H: Fluorescent staining for metabolically active cells and dead nuclei after 30 days of continuous perfusion in the bioreactor. Ru-CPOx beads emit orange. Bar=100 pm. I: Log-scale gene expression analysis of HepG2/C3A cells in static culture compared to those perfused for 30 days. PXR and CYP3A4 expression shows a 5- and 36-fold increase in the bioreactor, respectively. J: Cells exposed to 1% DMSO for 30 days show marked elevation of PXR and its target genes CYP2C9 and MRP3.
Figure 2B:
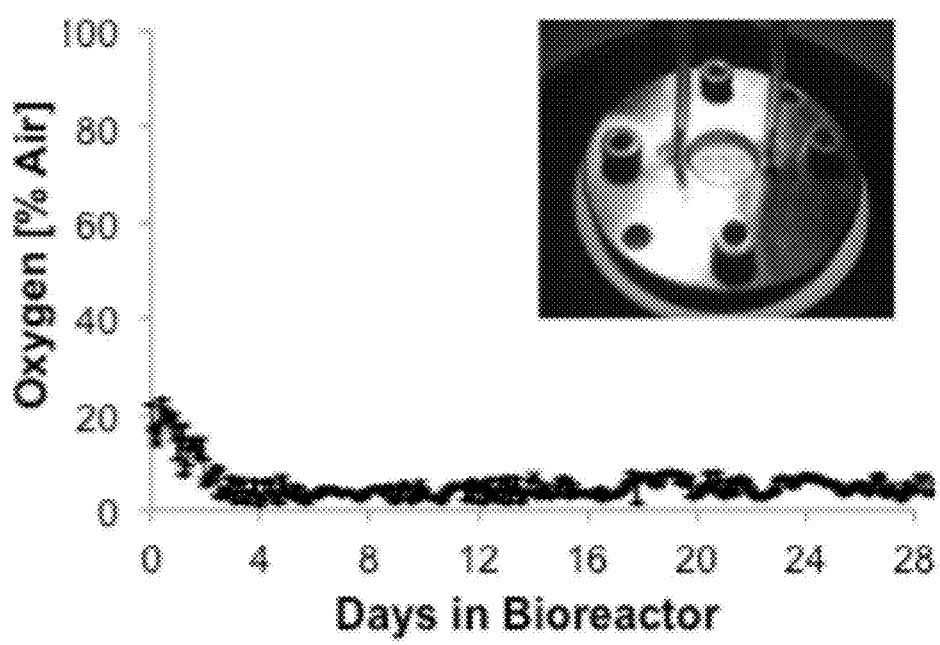

In another embodiment, the oxygen measuring ability of the system described herein is independent of optical focus, thereby permitting rapid high-throughput screening of hundreds of wells with little delay for focus acquisition and relatively simple robotic setups (FIG. 1G). In another embodiment, the oxygen sensor of the system of the invention is insensitive to amplitude (FIG. 1E-G). Accordingly, processes such as cell migration, aggregation, and necrosis that change the number and location of microbeads during the experiment have no effect on measurement stability permitting continuous measurements of oxygen uptake for over 28 days in vitro (FIG. 2B).

In another embodiment, integration of microscale sensors in the system described herein permits the continuous monitoring of cellular viability in a high throughput manner, minimizing the number of cells in each sample.

Thus, the present invention provides a perfusion microfluidic bioreactor system and a method for real time monitoring of one or more physiological parameters of a cell, including but not limited to mitochondrial respiration. In another embodiment, the system and method of the invention provide a stable platform for long-term maintenance of cells (e.g., liver cells) in an in vivo-like microenvironment, coupled with non-invasive ambient oxygen sensing. Thus, the invention provides an advantageous tool for in vitro toxicology. In exemplary embodiments, the oxygen sensor of the invention detects transient sub-threshold effects of toxins.

According to another embodiment, the invention provides a perfusion bioreactor system comprising:
a) a connector for connecting a chip to a perfusion element for flowing a perfusion medium in a controlled manner through the chip to provide shear force and nutrient supply;
b) a disposable chip adapted for holding the cells to be tested, and protecting them from shear force of the perfusion medium;
c) a sensing modality comprising elements selected from:
(i) an oxygen sensor being in a nanoparticulate form; or
(ii) at least two of the following sensors; a glucose sensor; a lactate sensor; an oxygen sensor.

The term "perfusion bioreactor" as used herein means a fluidized-bed reactor for cell culture designed for continuous operation as a perfusion system, i e, a system in which fresh medium is fed to the bioreactor at the same rate as spent medium is removed.

Typically, the chip may have a plurality of micro-wells. In another embodiment, the chip has one or more micro-channels orthogonal to the direction of flow of the perfusion medium. In some embodiments, each micro-well or micro-channel has a diameter of 75 to 3000 micrometers. In another embodiment, each micro-well or micro-channel has a height of 25 to 1000 micrometers. In another embodiment, the chip is flat-faced. The cells may be introduced by perfusion into a closed microchip. Alternatively, cells may be directly seeded on an open chip, and the chip subsequently closed for perfusion.

In an exemplary embodiment, the system of the invention has one or more sensing modalities. In one embodiment, the sensing modality is at least an oxygen sensor. In another embodiment, said oxygen sensor has a nanoparticle form. Typically, the size of the oxygen sensing nanoparticle is 50 nano-meters to 100 micro-meters. In particular embodiments, the oxygen sensor particle has a diameter in the range of 25-100 micro-meters, preferably 50 micro-meters.

In another embodiment, said oxygen sensor is a fluorescent or phosphorescent particle. In one embodiment, said oxygen sensor is a ruthenium-based molecules. In an exemplary embodiment, said oxygen sensor is a ruthenium-phenanthroline-based molecule. None limiting examples of ruthenium-based molecules include ruthenium-tris-4,7-diphenyl-1,10-phenanthroline ($[Ru(dpp)_3]^{2+}$), ruthenium(II)-tris(1,10-phenanthroline) ($[Ru(phen)_3]^{2+}$), dichlorotris(1,10-phenanthroline) ruthenium (II) hydrate, and ruthenium tris(2,2'-dipyridyldichloride)hexahydrate. In an exemplary embodiment, the oxygen sensor particles are 50 μm diameter polystyrene microbeads loaded with ruthenium-phenanthroline-based phosphorescence dye.

In another embodiment, said oxygen sensor is a metalloporphyrin-type molecules. In yet another embodiment, said oxygen sensor is selected from a fluorescein compounds, a polycyclic aromatic hydrocarbons, and/or any organic compounds having oxygen measuring capabilities. In another embodiment, said oxygen sensing particles comprises one or more elements selected from osmium, palladium, platinum, iridium, and copper.

In another embodiment, said oxygen sensing particles are adapted for being embedded in the cells (e.g., the three-dimensional layer, the cellular aggregate or the orgonoid) grown within the micro-well. In another embodiment, said oxygen sensing particles are placed in the micro-wells. In another embodiment, said oxygen sensing particles are combined (or mixed) with the cells to be tested in the micro-wells of the chip of the invention. One skilled in the art would appreciate that the number of oxygen sensing particles within each micro-well will depend on the type of sensor used. In embodiments wherein the oxygen sensing particles are ruthenium-phenanthroline-based molecule, the cells to oxygen sensing particles ratio is about 10,000-250,000 cells to 4-50 oxygen sensing particles, per micro-well. In an exemplary embodiment, the cells to oxygen sensing particles ratio is about 100,000 cells to about 20 oxygen sensing particles per micro-well. In another embodiment wherein the oxygen sensing particles are ruthenium-phenanthroline-based molecules, at least 3 particles are required for each field of view.

In another embodiment the sensing modality is composed of at least two of oxygen, lactate and glucose sensors. In another embodiment the sensing modality is composed of oxygen, lactate and glucose sensors.

In another embodiment, each of the three sensors may be independently electrochemically operated, or alternatively each of the sensors may be composed of nanoparticles typically fluorescent or phosphorescent. In one embodiment the oxygen sensor is made of nanoparticles and the lactate and/or glucose sensors are electrochemical. In another embodiment all three types of sensors are nanoparticles. In another embodiment, one or more of the oxygen, lactate and glucose sensors are integral to the system.

Sensors which are of fluorescent or phosphorescent particles (whether oxygen, lactate or glucose) may be detected by change of at least one of the following parameters: (a) frequency shift, (b) phase shift, (c) or amplitude shift.

In one embodiment, the oxygen sensor is the sole biosensor and is typically be fluorescent or phosphorescent particles and oxygen is detected by change of at least one of the following parameters: (a) frequency shift, (b) phase shift, (c) or amplitude shift (FIG. 1A-F). In a particular embodiment, the oxygen sensor of the system and method of the invention is used to measure decay time.

Typically, the system of the invention has a flow inlet, for providing medium and a flow outlet for withdrawing medium to and from the chip. In en exemplary embodiment, the glucose and/or lactate sensors are present on the flow outlet (FIG. 1G).

In one embodiment, the perfusion element is separate from the system, and the system of the invention has a connector or adaptor for connecting to the perfusion element. In another embodiment, the perfusion element is an integral part of the system of the invention. The perfusion element may be controlled by an external computer and in this case have a connector, or adaptor for connecting to the computer, or alternatively the system may have the computer as an integral part thereof.

In another embodiment, the cells within the system of the invention are kept under physiological conditions, such as by controlling perfusion rate, shear force and oxygen supply. One skilled in the art would appreciate that the required physiological conditions will vary depending on the examined cell type(s). As a non-limiting example primary hepatocytes consume oxygen at a rate of 0.3-0.9 nmol/sec/$10^6$ cells.

In another embodiment, said shear force applied on the cells is below 5 Pa, below 4 Pa, below 3 Pa, below 2 Pa, below 1 Pa, below 0.9 Pa, below 0.8 Pa, below 0.7 Pa, below 0.6 Pa, below 0.5 Pa, below 0.4 Pa, below 0.3 Pa, below 0.2 Pa, or below 0.1 Pa inside said micro-well. In another embodiment, the perfusion rates are of about 2-50 μl/min, about 3-40 μl/min, about 4-30 μl/min, about 5-25 μl/min, about 5-20 μl/min or about 10 μl/min. In another embodiment, the system provides a cell to volume ratio which allows substantial sensing of oxygen, glucose and/or lactate.

In another embodiment, the system further comprises at least one of the following components: an electronic control unit for signal modulation and read-out, an LED for excitation (e.g., of the oxygen sensing particles), an optical filter set (e.g., 531/40, 555, 607/70 nm) and a detector unit containing a photomultiplier (PMT). One skilled in the art would appreciate that the bioreactor can be excited by various wave lengths depending on the specific oxygen sensing particles used. Accordingly, emission may be read at various wave lengths as well. In a particular embodiment wherein the oxygen sensing particle is a ruthenium-phenanthroline-based particle, the bioreactor is excited by 532 nm and a 605 nm emission is read, so as to measure phosphorescence decay in real time.

In another embodiment, the system of the invention comprises live cells present on the disposable chip. In another embodiment, at least 75%, at least 80%, at least 85%, at least 90%, or at least 95% of said cells or viable cells.

In one embodiment, said cells are hepatocytes. The system may comprise two or more types of cells mixed together, for example hepatocytes and non-parenchymal cells, including but not limited to hepatic stellate cells, hepatic sinusoidal endothelial cells, and hepatic Kupffer cells.

In another embodiment, different cell types are placed in different wells, channels or chambers, mimicking different organs. For example, hepatocytes (mimicking a liver), cardiomyocytes (mimicking a heart), nephrons (mimicking a kidney), enterocytes (mimicking a intestine), neurons (mimicking a nerve system) or other cells in accordance with the desired usage loaded on the same microchip.

In another embodiment, different cell types can also be mixed with supporting cells, for example cardiomyocytes and meschnymal cells (e.g., fibroblasts, endothelial cells).

The cells may be placed on the microchip by any manner known in the art such as pipeting, placing or perfusing cells on the system as defined above.

In embodiments wherein the oxygen sensing particles are present in a separate container, they can be added to the system together with the addition of the cells.

According to another aspect, the invention provides a method for testing the effect of a substance of interest on one or more physiological parameters of cells, the method comprising:
  (i) providing the system of the invention;
  (ii) introducing cells to the micro-well of said system together with said oxygen sensing particles;
  (iii) introducing the substance of interest to the chip; and
  (iv) monitoring changes in oxygen uptake by said cells, thereby testing the effect of a substance of interest on one or more physiological parameters of cells.

In another embodiment, the system comprises a glucose sensor and/or a lactate sensor. In another embodiment, the method further comprises monitoring changes in glucose and/or lactate parameters. In another embodiment, said monitoring oxygen, glucose and/or lactate indicate changes in mitochondrial respiration of the examined cells.

In another embodiment, the substance to be tested is a substance for use in the cosmetic, pharmaceutical, food or agriculture industry.

According to another aspect, the invention provides a kit comprising (i) a disposable chip comprising one or more micro-wells adapted for holding cells and forming a tissue; and (ii) one or more oxygen sensing particles, and optionally one or more sensors selected from a glucose sensor and/or a lactate sensor.

In one embodiment, the oxygen sensing nanoparticles are present a priori on the chip (i.e., in one or more micro-wells). In another embodiment, the oxygen sensing nanoparticles are present in a separate container and added to one or more micro-wells of the chip when the cells are added to the micro-wells.

Monitoring Mitochondrial Respiration

Figure 3A:
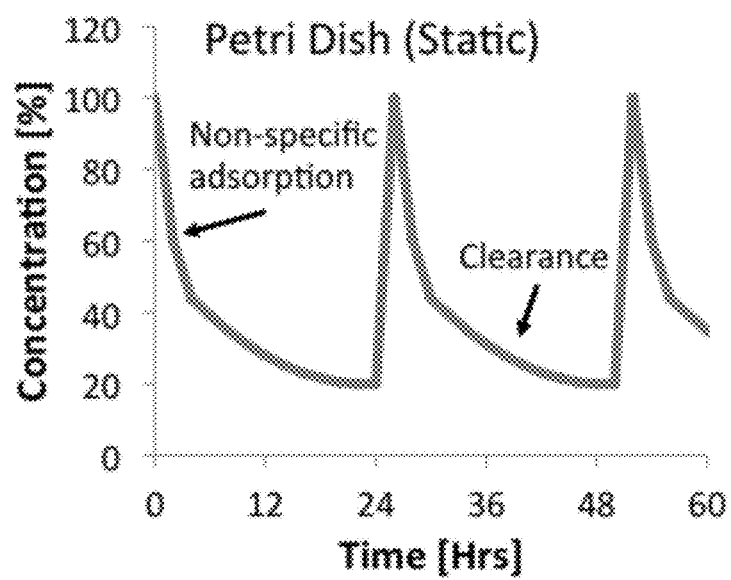
FIGS. 3A-G. A-B: Schematic of concentration over time curves in static cultures and perfused bioreactors. Concentrations of nutrients and stimuli in static cultures drop due to non-specific adsorption and consumption, while perfused bioreactors maintain a constant stimulation. C: Oxygen uptake over time response of HepG2/C3A cells exposed to increasing concentrations of amiodarone. Time to onset of mitochondrial damage is dose-dependent starting after 15, 6, and 2 hr for exposure of 0.2, 0.5, and 1 mM amiodarone, respectively. D: Dose dependence of amiodarone after 24 hours. $TC_{50}$ was calculated to be 425 pM. E: LipidTox™ staining shows a strong induction of phospholipidosis and accumulation of microvesicular steatosis following 24 hr exposure to 200 pM amiodarone. F: Intracellular lipids increased by 2-folds following exposure to amiodarone (p<0.001,n=4). G: Phospholipidosis increased by 2.5-folds following exposure to amiodarone (p<0.001,n=4).
Figure 3B:
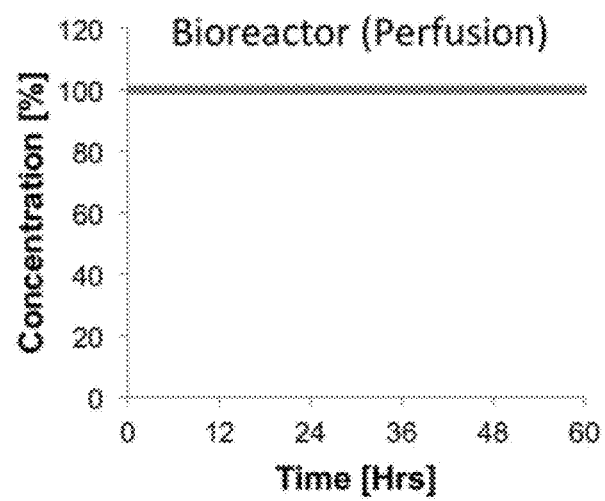
Figure 3C:
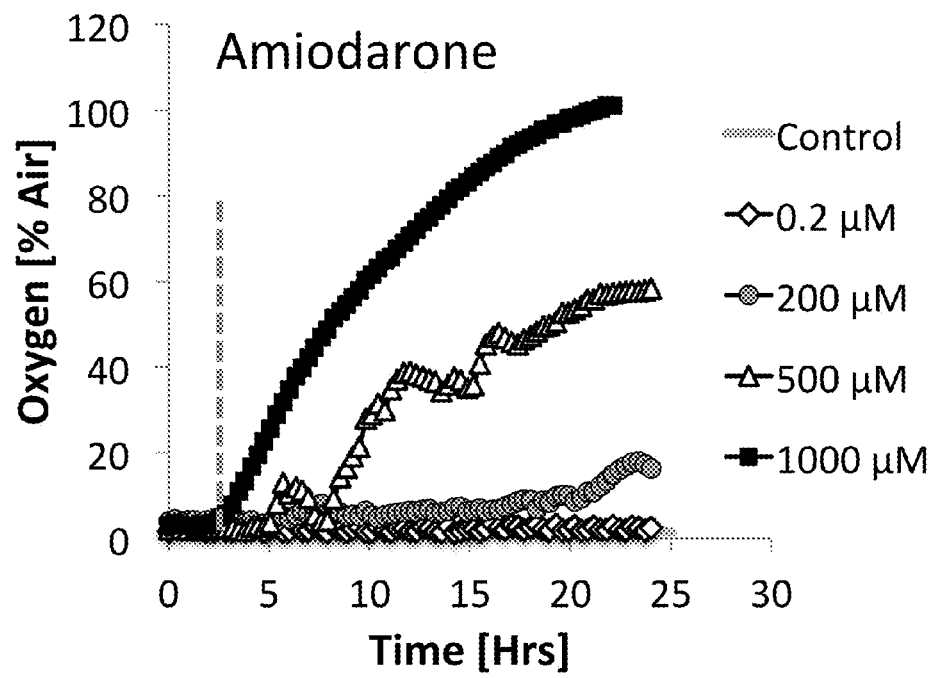
Figure 3D:
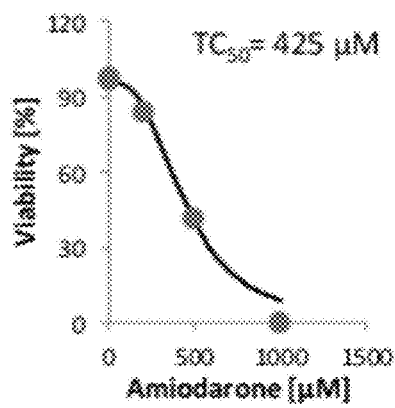

The system and method disclosed herein provides, in some embodiment, an ability to monitor mitochondrial respiration in real-time, thereby allowing to trace viability vs. time curves for each drug concentration (FIG. 3C, 4A), while drug concentrations are held stable by continuous perfusion (FIG. 3A,B). The dynamics of the response reveals important information on the drug mechanism of action, and the presence of short-lived sub-threshold effects of the drug. For example, while cell death is classically dose-dependent, the time to response is seldom measured. As demonstrated herein below, the onset of mitochondrial damage induced by amiodarone is dose-dependent, starting after 15, 6, and 2 hr from exposure at 0.2, 0.5, and 1 mM amiodarone, respectively (FIG. 3C). The dynamics of this response suggests the accumulation of a toxic intermediate, rather than direct damage of the parent compound. Indeed, the exemplified analysis shows a >2-fold increase in phospholipidosis and microvesicular steatosis (FIG. 3). In some embodiments, the invention may rapidly (about 24 hours) indicate microvesicular steatosis (as opposed to a lengthy 14 days exposure using other systems).

Further exemplified below, is a respiration vs. time curve of acetaminophen, which was dramatically different from amiodarone. Acetaminophen is known to cause hepatic injury through the generation of N-acetyl-p-benzoquinone imine (NAPQI) by CYP2E1 and CYP3A4. NAPQI is deactivated by conjugation with glutathione, but upon glutathione depletion, it irreversibly binds mitochondrial proteins leading to apoptosis and necrosis. However, prolonged use of acetaminophen can cause nephrotoxicity and epidermal necrolysis, but the molecular mechanisms of these injuries are not well understood Interestingly, early work showed that acetaminophen, like NAPQI, can cause reversible loss of oxygen consumption in isolated rat mitochondria. The studies showed the effect was abrogated by succinate, suggesting targeting to mitochondrial complex I in rodents. Regretfully, both studies used crude mitochondria preparations and Clark type electrodes that did not permit the acquisition of kinetic data.

Figure 4A:
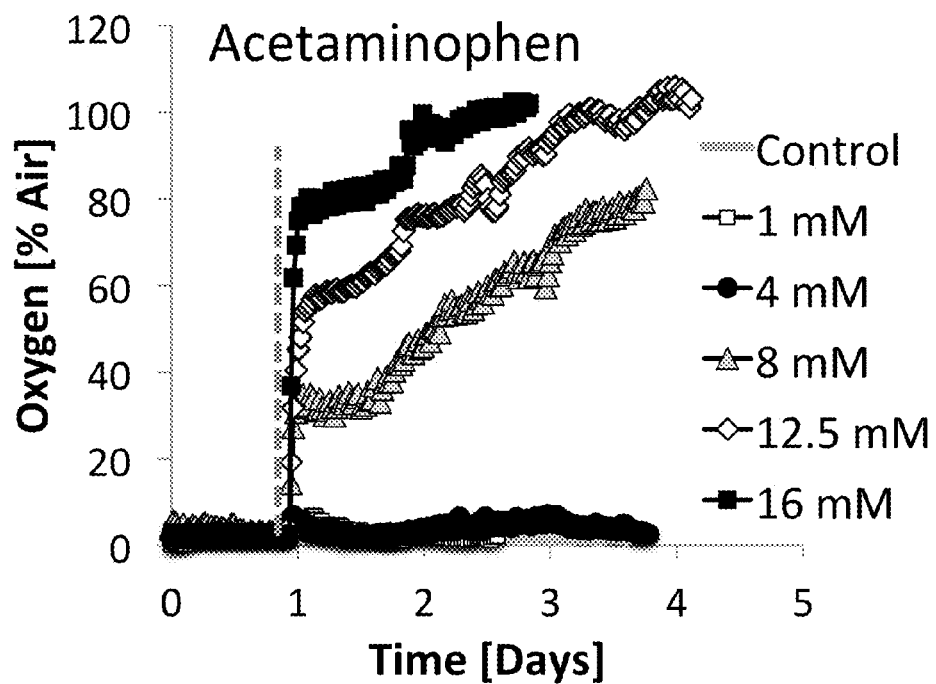
FIGS. 4A-L. A: Oxygen uptake over time response of HepG2/C3A cells exposed to increasing concentrations of acetaminophen. Two-phase response can be seen. An immediate dosesdependent loss of oxygen uptake culminating within 60 min, and a slow progressive dose-independent loss of oxygen uptake terminating with total cell death within 4 to 5 days. B: Temporal close up of (A) showing the immediate response occurs within minutes of exposure (t=0 hrs) for all concentrations measured. C: Dose dependence of acetaminophen after 12 hours. $TC_{50}$ was calculated to be 12.3 mM. D: Temporal close up of (A) shows a transient loss of mitochondrial respiration at 1 and 4 mM acetaminophen, below concentrations at which cell death could be detected. E: TUNEL™ staining shows massive apoptosis following 24 hr exposure to 8 mM acetaminophen. F: Apoptotic index is increased by 15-folds following exposure to acetaminophen (p<0.001,n=5). G: Two consecutive washout experiments (arrows) show a fast 35±5 min recovery during the early phase of response to 12.5 mM acetaminophen. H: Washout experiment (arrow) shows a slow 22 hr recovery during the late, progressive phase of response to 12.5 mM acetaminophen. I: Oxygen uptake over time response of HeLa cells exposed to 12.5 mM acetaminophen. Preincubation with 20 mM succinate did not affect HeLa response to acetaminophen, however incubation with 2 mM ascorbate and 0.5 mM TMPD abrogated the toxic response. J: Schematic of the mitochondrial electron transfer system illustrating the effect of acetaminophen on complex III. TMPD acts as an electron donor for cytochrome C, which cannot be reduced by the dysfunctional complex III. Ascorbate maintains TMPD in a reduced state. K: Oxygen uptake over time response of HeLa cells exposed to 10 μM antimycin A, a chemical piscicide directly binding cytochrome C. Preincubation with 2 mM ascorbate and 0.5 mM TMPD abrogated the toxic response. L: IVIVC curve comparing $TC_{50}$ values of primary human hepatocytes to our bioreactor showing an excellent $R^2$=0.99 correlation for acetaminophen, amiodarone, troglitazone, and rotenone.
Figure 4B:
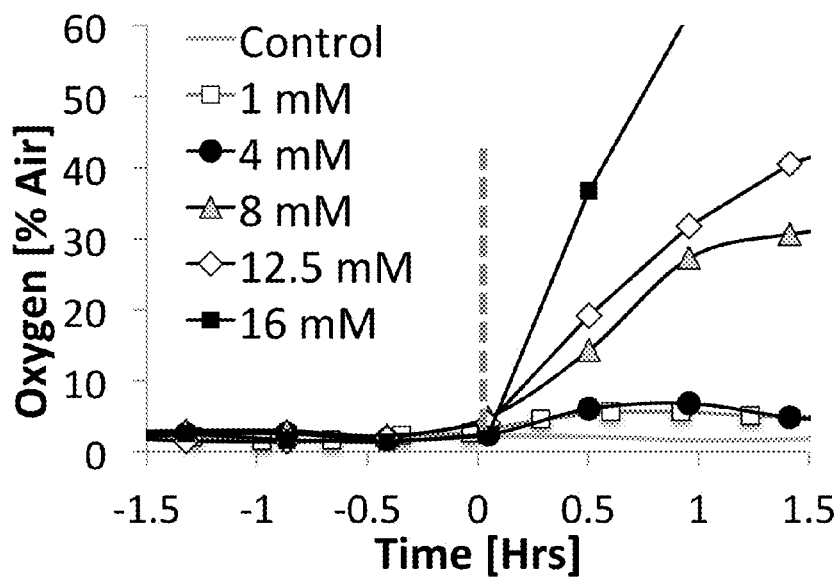
Figure 4C:
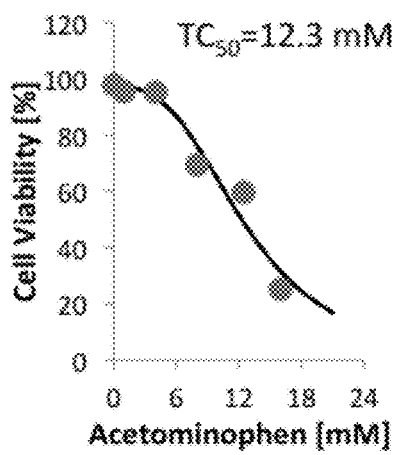
Figure 4D:
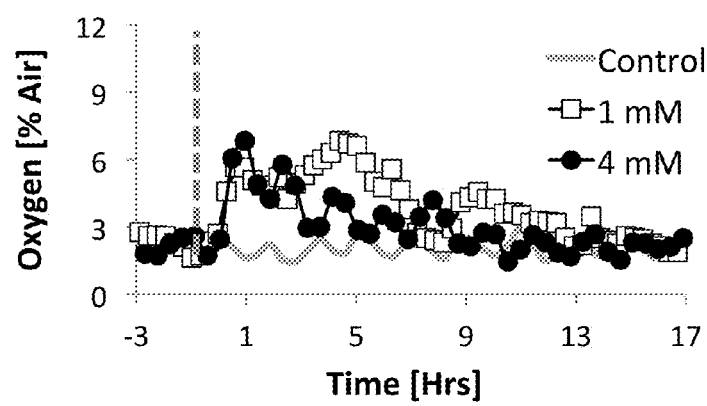
Figure 4E:
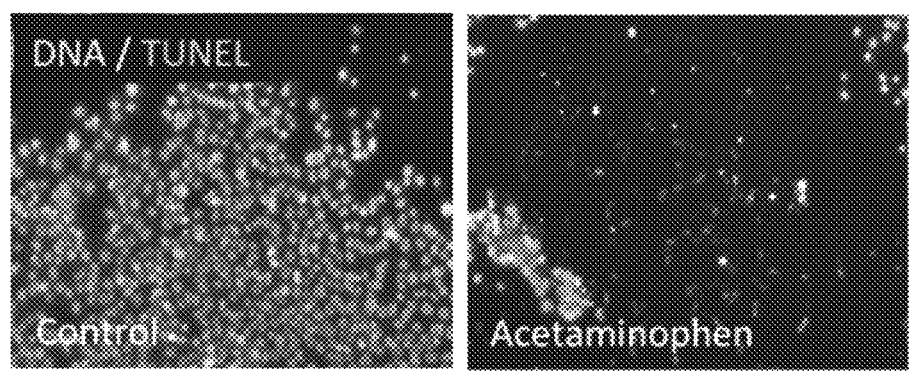
Figure 4F:
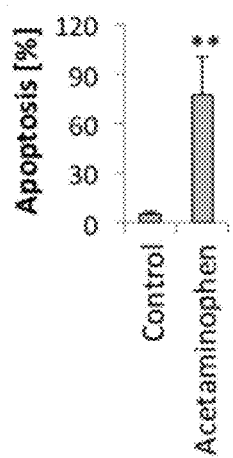
Figure 4G:
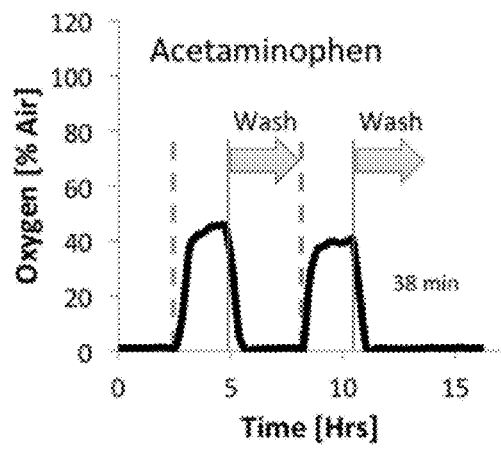
Figure 4H:
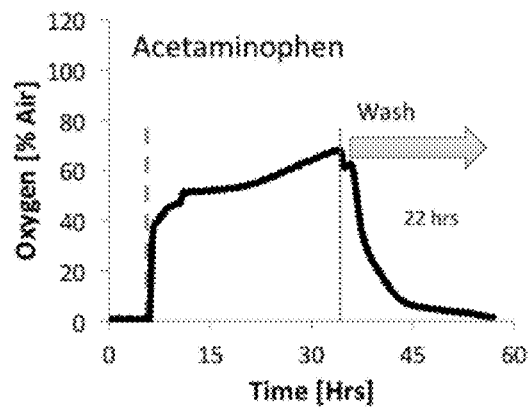
Figure 4I:
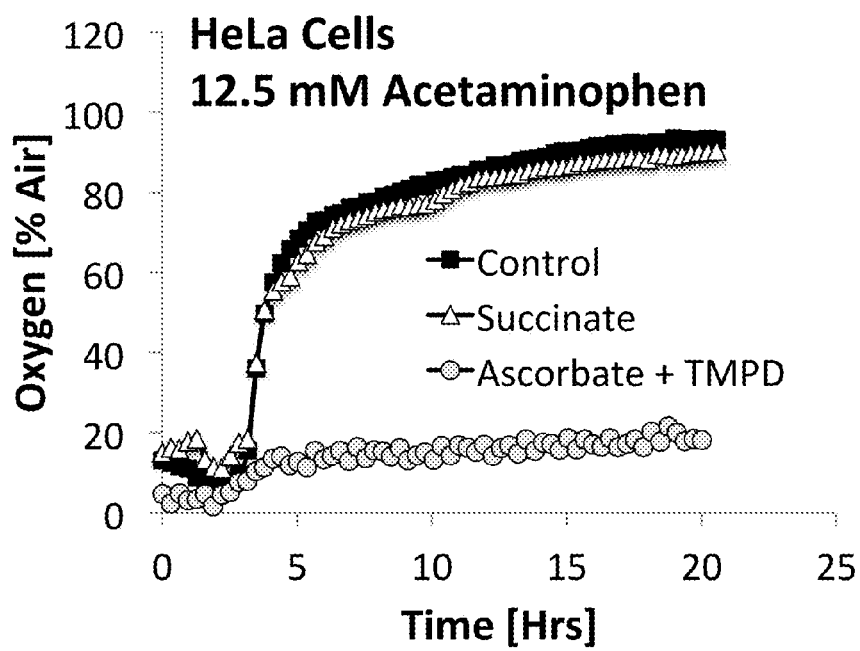

As exemplified herein below, acetaminophen exposure was followed by an immediate, but reversible loss of mitochondrial respiration in human cells (FIG. 4A,B). In fact, the sensitivity of our LBLQ measurement allowed detection of critical but short-lived sub-threshold effects of acetaminophen at 1 mM, before any toxic response could be observed (FIG. 4D). The dynamics of the response to acetaminophen confirmed a direct damage mediated by the parent compound, as there is not enough time for a toxic metabolite to accumulate. Indeed, the analysis presented herein shows that HeLa cells, that do not express CYP2E1 or CYP3A4, show an identical immediate loss of mitochondrial respiration upon exposure to acetaminophen (FIG. 4I). Further analysis demonstrated that acetaminophen directly affects mitochondrial complex III in human cells.

The second phase of acetaminophen toxicity showed a slow progressive loss of mitochondrial respiration starting 60 min after exposure and terminating with cell death (FIG. 4A). Interestingly, the second phase was concentration independent, suggesting the limiting factor was the expression of CYP2E1 and CYP3A4 by our HepG2/C3A cells. Indeed, this second step was absent in HeLa cells, suggesting it is mediated by hepatic NAPQI production (FIG. 4I). This step appeared to be irreversible, with cell proliferation producing a prolonged recovery within 22 hrs (FIG. 4H).

EXAMPLES

Materials and Methods

Reactor fabrication. The microwell bioreactors were fabricated of stainless steel by CNC machining. The two circular support structures had a diameter of 50.8 mm and were equipped with milled recesses, forming the inner compartment (40 µl) as well as the holder for incorporating the PDMS-based microwell unit (FIG. 2A). The reactor inlets, outlets and the flow channel compartment were located in the reactor top part. Both faces featured glass windows for inverted and upright microscopy. The lower glass slide (25 mm×25 mm×0.5 mm, W×L×H) also served as support for the PDMS-based microwell unit. The two reactor parts were screwed together and housed the internal removable PDMS well unit in which cells were cultured and, thus, protected from fluidic shear. Sealing around the microwells was realized with an o-ring (2-117, Parker, Berlin, Germany). The inlets and outlets were connected to a syringe pump and waste, respectively, using Tygon tubing with an inner diameter of 762 µm (Saint-Gobain, Paris, France).

Cell culture. The hepatoblastoma cell line HepG2 (ACC 180, German Collection of Microorganisms and Cell Cultures, DSMZ, Braunschweig, Germany) was cultured in Modified Eagle's medium (MEM, Biochrom, Berlin, Germany) supplemented with 10% v/v fetal calf serum (FCS), 100 U ml$^{-1}$ penicillin and 100 µg ml$^{-1}$ streptomycin (Biochrom, Berlin, Germany) in a cell incubator (Binder, Tuttlingen, Germany) at 95% relative humidity and 5% $CO_2$ supply.

PDMS-based microwell fabrication. The PDMS-based microwell unit (Sylgard 184, Dow Corning, USA) possessed nine microwells (ϕ 1.5 mm, h=500 µm) in a 3×3 configuration with a hole-to-hole distance of 3 mm. The unit was fabricated according to the applied pressure method [1] using SU8-phothoresist and silicon soft lithography. The fabrication was done in a standard class 100 clean room at the HUJI nanofabrication facility (Jerusalem, Israel). The PDMS-based well unit was firmly bonded to the glass support following oxygen plasma activation operating at an intensity of 90 W for 20 s (Diener PICO UHP, Ebhausen, Germany) after HF etching of the glass surface.

Reactor Seeding. The following steps of cell seeding and reactor assembly were carried out in a sterile hood. Prior to seeding cells into the reactor, the PDMS-based well unit and all tubings were cleaned and sterilized with 70% EtOH, washed with dd$H_2O$, dried and subsequently exposed to UV light for at least 30 min. The cells were detached from the tissue culture substrate with trypsin-EDTA (Biochrom, Berlin, Germany), counted, centrifuged at 280 rpm for 5 min at 4° C. and resuspended with 100 µl of collagen type I solution to a final density of 4×10$^6$ cells per device. During resuspension of the cells, 300 µg to 500 µg oxygen sensing beads (CPOx-50-RuP, Colibri Photonics, Potsdam, Germany) were added, resulting in at least ten to 20 beads per microwell after completion of the cell seeding protocol. The collagen type I solution was made of 560 µl dd$H_2O$, 100 µl PBS (10×), 6.25 µl of 1 N NaOH and 333 µl of collagen type I (3.6 mg ml$^{-1}$, BD Biosciences, San Jose, Calif., USA). The PDMS microwells were primed for 5 min on ice with this solution in order to eliminate air bubbles from the wells.

Subsequently, 100 µl of collagen type I suspension containing cells and oxygen-sensing beads was placed on top of the PDMS-based well unit, thus covering all nine microwells. The unit was kept in a sterile 50.8 mm petri dish placed on ice for 5 min in order to allow the cells to sediment into the wells. The low temperature prevented premature collagen polymerization and the induction of cellular stress response pathways. Afterwards, excess cell and microbead suspension was gently but thoroughly wiped off the PDMS-based well unit using a sterile glass coverslip (FIG. 2C) leading to a concentration of 100,000 cells/well. The inoculated well unit was then incubated for 5 min at 37° C. in a humidified cell incubator (see above) at 5% $CO_2$ in order to polymerize the collagen and by this immobilize the cells and microbeads in the wells. Following polymerization, the well unit, loaded with the cells, was immersed in 5 ml of MEM medium (composition see above) for 20 min at 37° C. in a cell incubator (see above). Subsequently, the PDMS-based well unit was transferred into the bioreactor. After sealing, the bioreactor was placed into the climate control chamber (37° C., ACUO$_2$, Evotec, Germany) of an inverted fluorescence microscope (IX81, Olympus, Japan) and perfused with MEM (composition see above) supplemented with 10 mM HEPES with a flow rate of 10 µl min$^{-1}$ using a syringe pump (Harvard Apparatus, USA). The automated and motorized microscope stage was equipped with a holder for three microreactors, allowing for performing three experiments simultaneously.

Chemical compound injection. The cells in the reactor were exposed to four concentrations of amiodarone (Sigma Aldrich, Schnelldorf, Germany, 0.2 µM/200 µM/500 µM/1 mM) or acetaminophen (Sigma Aldrich, Schnelldorf, Germany, 4 mM/8 mM/12.5 mM/16 mM) causing different drug-induced patterns of hepatotoxicity. Amiodarone was dissolved in DMSO to a stock concentration of 50 µM, leading to final medium concentrations between 4×10$^{-4}$-2%. Acetaminophen was dissolved in cell culture medium to the given concentrations. Amiodarone was used as a compound for modeling cholestasis, whereas acetaminophen was employed for inducing an apoptotic response. In order to further elucidate the cytotoxic mode of action of acetaminophen (mitochondrial dysfunction), cells were also treated with acetaminophen (12.5 mM) combined with either succinate (20 mM), or N,N,N',N'-Tetramethyl-p-phenylenediamine (TMPD, Sigma Aldrich, Schnelldorf, Germany, 0.5 mM) in combination with ascorbate (Sigma Aldrich, Schnelldorf, Germany, 2 mM). Succinate as the substrate for complex II was used as an electron donor for the putatively toxicologically affected complex I in the mitochondrial electron transfer system (ETS), whereas TMPD was used to donate electrons to cytochrome c in order to test for a putative toxicological effect on complex III in the ETS. Ascorbate was used to maintain TMPD in a reduced state. The cytotoxic effects were evaluated by real-time monitoring of the change in oxygen consumption and for subsequent confirmation of the toxicological endpoints also by specific conventional staining assays (see below).

Toxicity Mode of Action Assays.

Lipid Accumulation Disorders: Steatosis and Phospholipidosis.

Steatosis and phospholipidosis were evaluated using the HCS LipidTOX™ system (Life Technologies, USA) according to manufacturer directions. Briefly, cells were incubated with green neutral lipid and red phospholipidosis dyes and counterstained with 1 µg/mL Hoechst 33342 for 30 min, and washed with PBS. LipidTOX green and red staining intensity were normalized to number of Hoechst-labeled nuclei.

Apoptosis

Figure 3E:
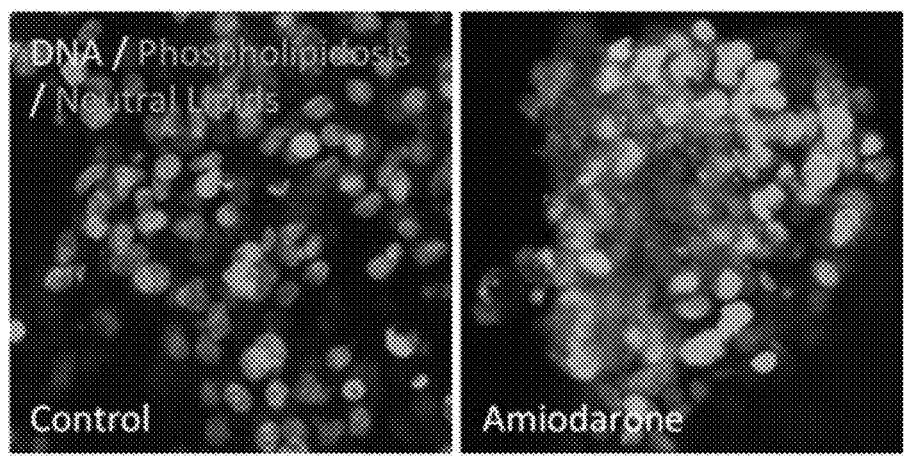

Quantification of apoptotic cells in the reactor was performed utilizing the DeadEnd Fluorometric TUNEL System (Promega, Madison, Wis., USA) (FIG. 3E,F). This system catalytically incorporates fluorescein-12-dUTP at 3'-OH DNA ends utilizing the enzyme terminal deoxynucleotidyl transferase (TdT). Cells in the reactor were exposed to 12.5 mM acetaminophen or MEM medium alone (control) under a constant flow rate of 10 μl min$^{-1}$ for 24 h. Subsequently, the PDMS-based unit was removed from the reactor and the cells in the unit were fixed with 4% formaldehyde in PBS for 30 min at 4° C. After three washing steps with PBS, the cells were permeabilized with 0.2% Triton X-100 in PBS for 5 min. After additional three washes, the cells were equilibrated at room temperature for 10 min with equilibration buffer and then treated with TdT reaction mixture for 60 min at 37° C. The reaction was stopped using 2×SSC for 15 min.

Oxygen measurement. Real-time oxygen measurements were performed optically by means of phosphorescence quenching. Biocompatible polystyrene microbeads with a diameter of 50 μm equipped with a ruthenium-phenanthroline-based phosphorescence dye (CPOx-50-RuP, Colibri Photonics, Potsdam, Germany) were used as microprobes and were coimmobilized with the cells (FIG. 1D) in the collagen matrix during reactor seeding (described above). The electronic measurement system (OPAL, Colibri Photonics, Germany) comprises a control module, an LED as the excitation source and a detector unit (FIG. 1A). The latter contains a photomultiplier (PMT) which was mounted on one of the oculars of an inverted fluorescence microscope (IX81, Olympus, Japan) by means of an ocular adapter tube (Di-Li Mikroskope+Geräte, Germany). Thus, the camera port was kept available for imaging. The LED was connected to an excitation light guide of the microscope. The latter was furthermore equipped with a 531/40, 555, 607/70 nm optical filter set. Excitation light in the green spectrum is preferable for use, since violet and blue light induces photochemical side reactions in cell culture media, likely triggered by riboflavin. Briefly, the phosphorescence signal of the probe is emitted with a delay given by the lifetime of the excited triplet state $T_1$ of the dye molecule (FIG. 1B). Oxygen acts as a quencher of the phosphorescence, leading to a decrease of the decay time and the signal intensity with increasing concentration. A major benefit of using the phosphorescence decay time and not the signal intensity is that decay times do not depend on probe concentration, excitation intensity or depth of the focal plane. To determine phosphorescence decay times in real time, phase modulation is a convenient technique. If excited with sinusoidally intensity-modulated light, the emission signal of the probes exhibits a shift in phase with respect to the excitation signal (FIG. 1C). The phase shift can be correlated to the decay time and in turn to the oxygen concentration in the direct microenvironment of the probes, featuring a high spatial resolution. A shortcoming of the standard phase modulation technique is its susceptibility to superimposition with in-phase background fluorescence, which alters the phase shift of the total signal. Especially if small and low-signal microprobes are used, the resulting errors become serious. Therefore, a special two-frequency phase modulation technique was applied. The simultaneous measurement of the respective phase shifts at two different modulation frequencies allowed for eliminating interfering background fluorescence and for separating of the actual phosphorescence signal. As modulation frequencies, 53.5 kHz and 31.3 kHz were chosen. Simultaneous measurement of five to ten microprobes and the use of their averaged overall signal sufficed to achieve a very low error in the detected dissolved oxygen concentration of 1% to 2% (FIG. 1E). This data was obtained by measuring the standard error for ten single beads at 0%, 50% and 100% dissolved oxygen in $H_2O$ with a subsequent combined error calculation routine (Mathematica, Wolfram, UK). Intensity changes did not affect the measurement. This allowed for long-term measurements in a living 3d micro cell culture environment, independent of the optical focus (FIG. 1F). For one measurement point, a single microwell of each reactor was illuminated for 3 s to 4 s in a 17 s interval over 100 s and the recorded measurement values were averaged. One measurement of each reactor was carried out every 15 min. Long-term constant illumination of the sensor particles over 24 h did neither show a drift of the phasing nor a relevant loss in signal intensity allowing for long-term measurements over several weeks.

COMSOL numerical simulation. A computational fluid dynamic (CFD) model was used to model shear stress magnitudes and oxygen consumption rate the cells experience within the microreactor. Tridimensional CFD simulations of the reactor were carried out by Comsol Multiphisics 4.3 a, coupling the stationary Navier-Stokes module for fluid-dynamics with the convection and diffusion model for oxygen transport. The entire volume of the bioreactor was meshed using tetrahedral elements of size 0.2 mm. The inlet oxygen concentration was set to 0.21e-6 mol/m$^3$ and the relevant fluidic parameters for the culture medium were made for 37° C., therefore the diffusion coefficients of oxygen was set to 1.8e-9 m$^2$/sec.

Quantitative Real Time Polymerase Chain Reaction (qRT-PCR). RNA was isolated and purified utilizing Macherey-Nagel NucleoSpin RNA II kit according to manufacturer instructions. RNA concentration and purity was determined using NanoDrop ND-1000 spectrophotometer (Thermo Fisher Scientific, USA). cDNA was synthesized from 1 μg RNA sample using qScript cDNA SuperMix (Quanta Biosciences, USA) according to the manufacturer protocol. Gene expression analysis was carried out utilizing KAPA SYBR FAST Universal 2X qPCR Master Mix (Kapa Biosystems, Boston, USA) on BioRad CFX96 Real-Time System (New South Wales, Australia), according to the manufacturer protocol. Gene transcription was evaluated using the ΔΔCt method normalized to 60S ribosomal protein L32 (RPL32) or ubiquitin C (UBC).

Example 1

Real-Time Focus Independent Measurement of Oxygen Uptake in Microfluidic Bioreactor Oxygen uptake is a critical measurement of mitochondrial function and metabolic activity (Green and Reed 1998; Han et al. 2013). To reliably measure oxygen on the microscale, a ruthenium-based dye whose fluorescence is quenched in the presence of oxygen was used. Regretfully, measurements of fluorescence intensity are affected by small changes in focus, particle migration, and cell movement making these types of probes unreliable for real time measurements. To overcome this difficulty, an optical system was designed in which a microfluidic bioreactor is excited by 532 nm LED (FIG. 1A), producing a triplet state T1 of the ruthenium dye (FIG. 1B). Oxygen acts as a quencher of the phosphorescence emission, leading to a decrease in decay time. A major benefit of measuring decay time over signal intensity is that the decay time is independent of probe concentration and excitation intensity. To measure this phosphorescence decay in real time, a sinusoidal intensity-modulated light was used, resulting in an oxygen-dependent phase shift in the 605 nm emission (FIG. 1C,D).

The sensitivity of the system described herein allows to make reliable measurements even when particles numbers change through the experiment, due to shear forces or cell movement, resulting in measurement error under 2% with as little as 4 particles per field of view (FIG. 1E). In fact, the sensitivity of the frequency-based phosphorescence system was so high; it could reliably measure oxygen concentration up to 1.3 mm away from the optical focus (FIG. 1F). This sensitivity permits precise oxygen uptake measurements in real time while actively moving from one micro-well to the next.

Example 2

Reactor Characterization and Long-Term Maintenance of Perfused Cell Culture

Figure 2C:
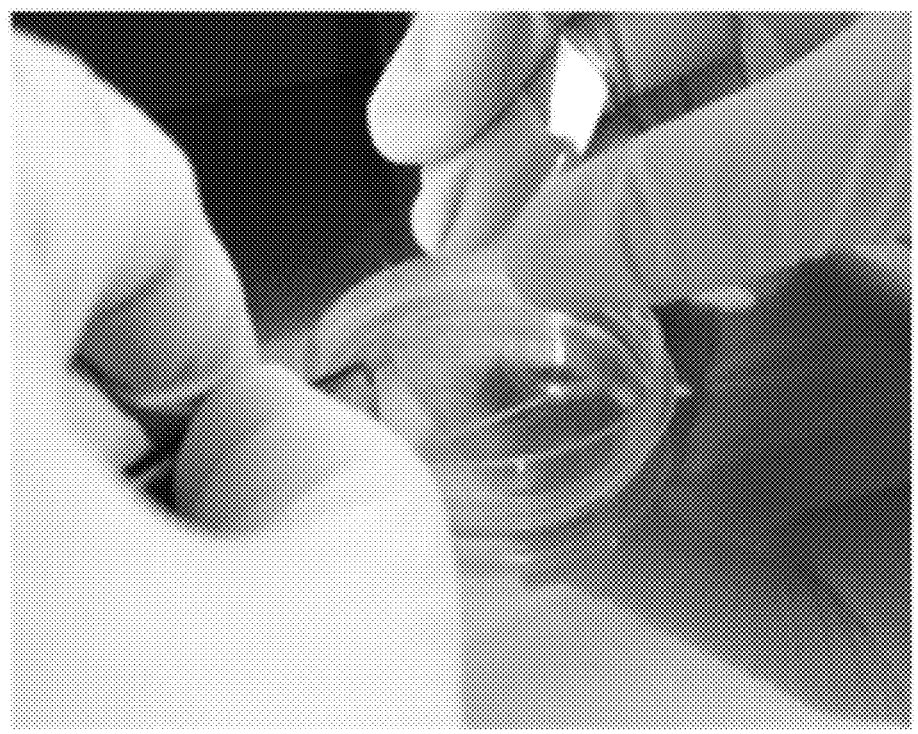
Figure 2D:
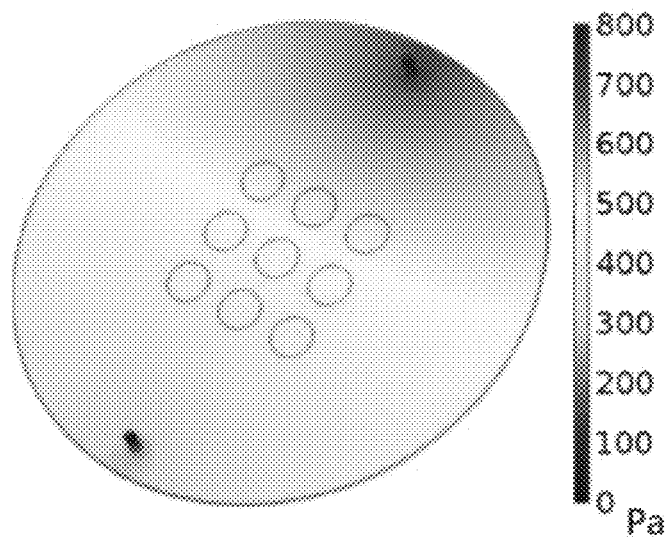
Figure 2E:
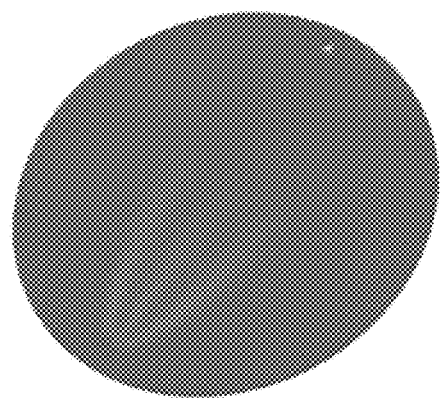
Figure 2F:
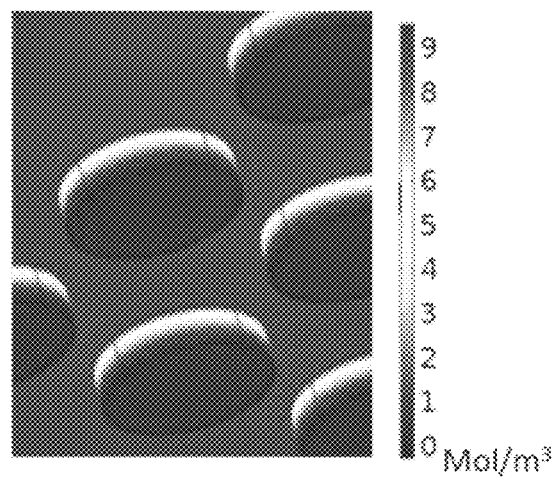
Figure 2G:
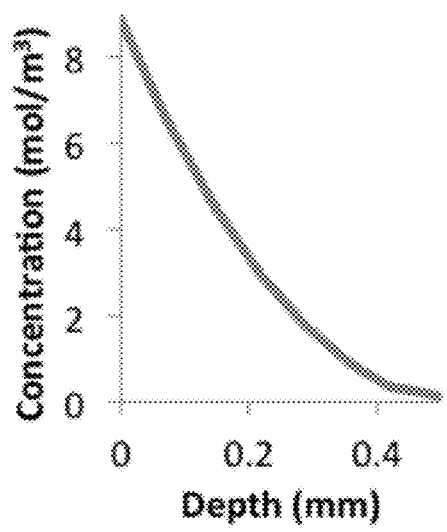

The liver is highly vascularized, delivering oxygen at rates of 0.9 nmol/sec/$10^6$ cells (Nahmias et al. 2006), while at the same time protecting hepatocytes from the negative effects of shear forces (Rowlands et al. 2014; Tilles et al. 2001). The gradient of oxygen that develops along the sinusoid is thought to induce a demarcation of function, termed metabolic zonation. To mimic this environment, a stainless steel bioreactor that fits standard 2" inserts was designed, with an internal compartment for a removable microwell insert (FIG. 2A,B). HepG2/C3A cells were mixed with oxygen probes and suspended in collagen gel prior to seeding directly in the microwell insert (FIG. 2C, 1D). The small diameter of the microwells leads to rapid aggregation, creating liver spheroids after overnight incubation. Cell viability was evaluated microscopically before the inserts were physically sealed in the bioreactor and perfused. Computation fluid dynamic modeling (FIG. 2D-G) showed physiological shear forces under 0.1 Pa inside the microwells for perfusion rates of 10 μl/min. The high flow rate resulted in similar oxygen concentration delivered to each well in the array (FIG. 2E,F). Oxygen consumption caused a gradient to develop along the perfused spheroid mimicking the in vivo microenvironment (FIG. 2G) (Baharvand et al. 2006; Cukierman et al. 2001).

Long-Term Maintenance of Perfused Spheroids

Figure 2H:
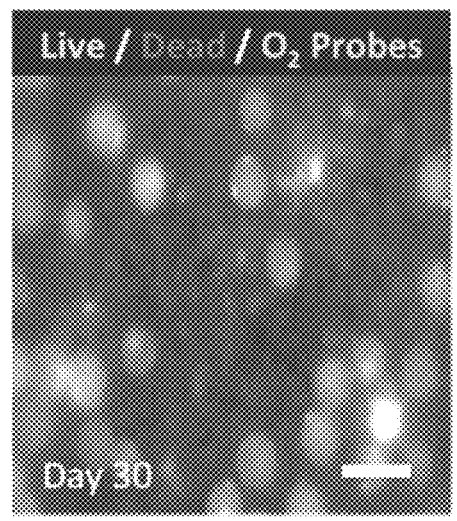
Figure 2I:
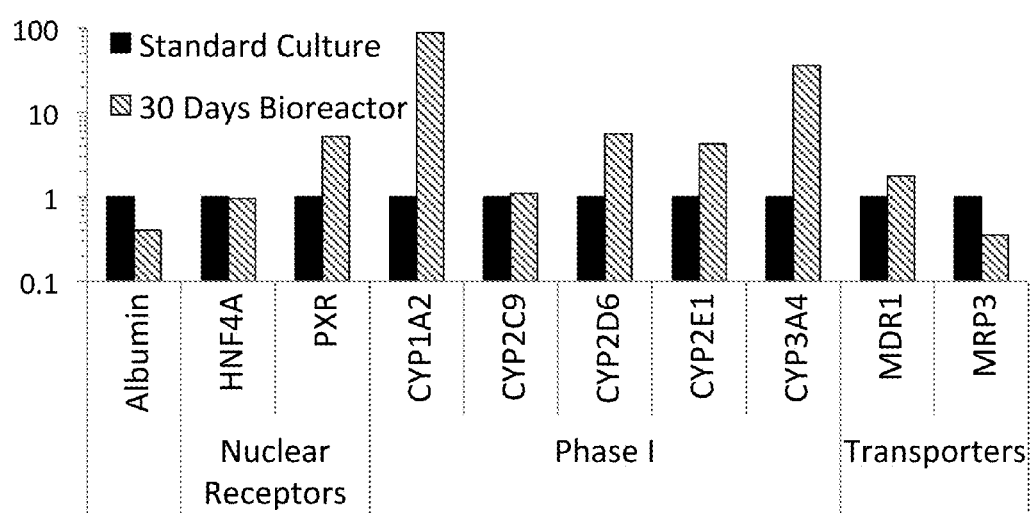
Figure 2J:
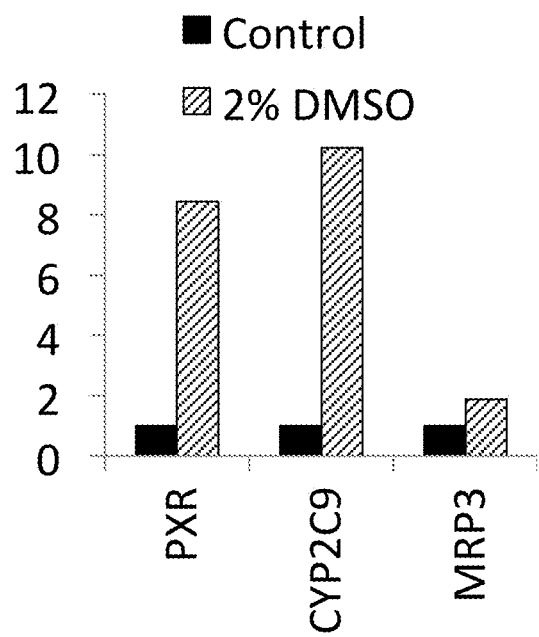

Physiologically perfused HepG2/C3A spheroids stabilized their metabolic activity within 48 hrs and their oxygen uptake rates remained stable for 28 days of continuous perfusion (FIG. 2B). Live-Dead staining showed greater than 98% viability following 28 days of perfusion (FIG. 2H). Quantitative gene expression analysis showed the elevation of liver-specific function in the microwell bioreactor (FIG. 2I). Specifically, the pregnane X receptor (PXR) that acts as a sensor for xenobiotics controlling the expression of CYP450 enzymes, exhibited a 5-fold higher expression compared to cells in static culture. CYP2E1 and CYP2D6 showed a similar 4- and 6-fold increase, respectively. Remarkably, CYP3A4 that is responsible for the clearance of 40% of the drugs on the market, showed a 36-fold higher expression than static culture (FIG. 2I). This level of CYP3A4 expression is 6% of primary hepatocytes, compared with 0.3% for HepG2/C3A in standard culture. Finally, continuous exposure of the HepG2/C3A spheroids to 1% DMSO for 28 days showed little affect on cell viability. However, gene expression analysis showed an 8-fold increase in PXR expression, and an associated 2- and 10-fold increase in its target genes CYP2C9 and MRP3, respectively (FIG. 2J).

Example 3

Long-Term Exposure to Amiodarone Induces Dose-Dependent Steatotic Injury

Figure 3F:
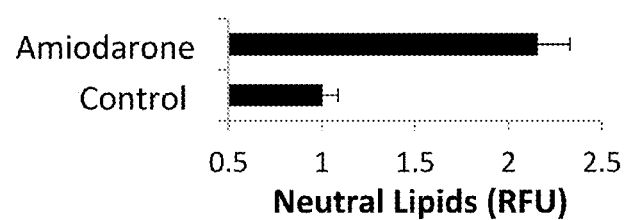
Figure 3G:
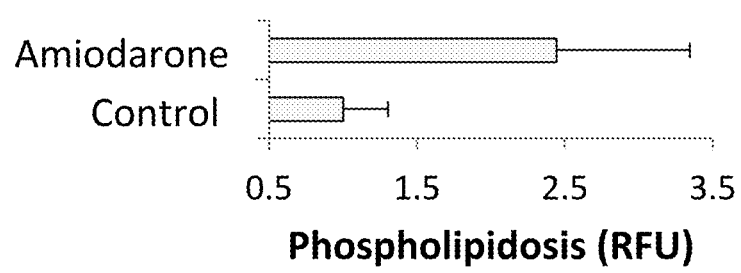

Amiodarone is an antiarrhythmic agent reported to cause phospholipidosis, as well as steatosis upon a longer exposure to the drug (Anthérieu et al. 2011; Lewis et al. 1989). Regretfully, while phospholipidosis can be readily identified in vitro, primary cells fail to accumulate lipid droplets in vitro following repeated exposure to amiodarone, possibly due to the short lifespan of the cells (Anthérieu et al. 2011). One benefit of perfused bioreactors is the ability to deliver stable drug concentrations, without the effects of metabolic clearance and non-specific absorption (FIG. 3A-B). Amiodarone was perfused at concentrations ranging from 200 nM to 1 mM for 24 hrs, and oxygen uptake of the cells was monitored in real-time to assess cell viability and metabolic function (FIG. 3C). Oxygen concentration (y-axis) remained unchanged at 200 nM amiodarone, not different from control. However, oxygen uptake dropped when cells were exposed to 200, 500, and 1000 μM Amiodarone, reaching 84%, 42%, and 0% of normal respiration following 24 hrs exposure, respectively. Interestingly, the onset of the response was similarly dose-dependent showing respiratory damage after 15, 6, and 2 hrs, respectively (FIG. 3C). The dynamics of this response suggests the accumulation of a toxic intermediate, rather than direct damage of the parent compound. Plotting the dose-dependent response of the amiodarone at 24 hr, a $TC_{50}$ of 425 μM was calculated in the system of the invention (FIG. 3D), compared with 100 μM in primary hepatocytes. Finally, to evaluate the toxicological end point of amiodarone, phospholipidosis and neutral lipid accumulation (i.e. steatosis) were stained while counterstaining for Hoechst (FIG. 3E). Cells exposed to amiodarone showed a 2.1-fold increase in intracellular lipids (p<0.001, n=4) and a 2.4-fold increase in phospholipidosis (p=0.02, n=4) (FIG. 3F-G).

Example 4

Long-Term Exposure to Acetaminophen Reveals CYP2E1-Independent Mitochondrial Toxicity Acetaminophen is a commonly used analgesic and antipyretic, with side effects considered mild to non-existent in safe dosing. However, acetaminophen overdose is the leading cause of acute liver failure in the Western World (Blieden et al. 2014). Acetaminophen toxicity is driven by CYP2E1 and CYP3A4-mediated production of the toxic metabolite, N-acetyl-p-benzoquinone imine (NAPQI). NAPQI creates protein adducts, damaging mitochondrial respiration, and activating a secondary inflammatory response (Blieden et al. 2014; Kaplowitz 2004a). Interestingly, acetaminophen is also documented to produce kidney necrosis as well as epidermal necrosis, by mechanisms that are not well understood (Halevi et al. 2000; Jones and Vale 1993).

Acetaminophen was perfused at concentrations ranging from 1 to 16 mM for 4 consecutive days, and oxygen uptake of the cells was monitored in real-time (FIG. 4A). Surprisingly, oxygen uptake rates dropped in all concentrations studied. Analysis of the kinetic data revealed two distinct phases: The first phase was characterized by a rapid loss of mitochondrial respiration starting seconds after exposure to acetaminophen and terminating within 60 minutes (FIG. 4B). This fast phase was characterized by a dose-dependent response, with HepG2 cells reaching 70%, 55%, and 25% of normal respiration within 60 minutes for 8, 12.5, and 16 mM acetaminophen, respectively (FIG. 4C). Remarkably, this rapid loss of mitochondrial respiration could also be detected below the threshold for toxicity in 4 and 1 mM acetaminophen, within the physiological range of the drug (FIG. 4D). In contrast, the second phase showed a slow, linear loss of oxygen uptake terminating with total cell death within 3 to 5 days. Interestingly, the second phase was concentration independent.

Plotting the dose-dependent response of acetaminophen at 12 hr, we calculate a $TC_{50}$ of 12.3 mM (FIG. 4C), compared with 4 to 8 mM in primary human hepatocytes. To evaluate the toxicological end point of acetaminophen, the number of intact and apoptotic nuclei was quantified using the TUNEL assay (FIG. 4E). Cells exposed to acetaminophen showed a 15-fold increase in apoptosis ($p<0.001$, $n=5$), as well as unlabeled cell death suggesting necrosis (FIG. 4F).

Figure 4J:
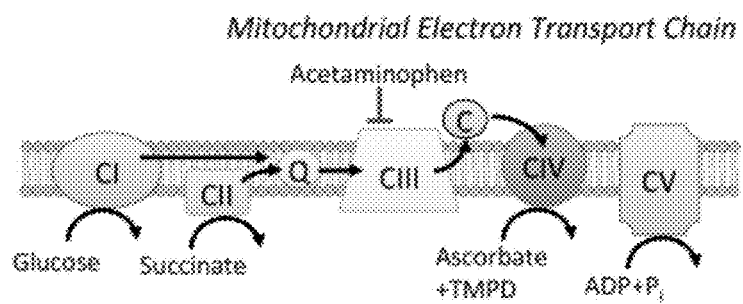

The immediate loss of mitochondrial respiration following exposure to acetaminophen during the first phase, suggests a direct effect of the parent compound on mitochondrial respiration, rather than NAPQI mediated damage. The inventors sought to examine whether the toxic effects are reversible. Interestingly, recovery during the rapid phase was fast, concluding in 35±5 min (FIG. 4G). However, recovery during the slow phase lasted over 20 hrs, allowing cell proliferation to restore function, suggesting a NAPQI-mediated irreversible effect (FIG. 4H). To evaluate this, the inventors exposed cervical cancer HeLa cells that do not express CYP2E1 or CYP3A4, and therefore cannot produce NAPQI in response to acetaminophen exposure (FIG. 4I). Surprisingly, HeLa cells showed an identical rapid loss of mitochondrial respiration immediately after exposure to acetaminophen and terminating in 60 min, but failed to display the second dose-independent phase of toxicity. The addition of succinate, a complex II reducing substrate, has no effect on the toxicity. However, the addition of ascorbate and N,N,N',N'-tetramethyl-p-phenylenediamine (TMPD), complex IV reducing substrate, eliminated the toxicity of acetaminophen in both HeLa and HepG2 cells (FIG. 4I). These results suggest that acetaminophen can directly affect mitochondrial complex III in a CYP450-independent mechanism (FIG. 4J).

Figure 4K:
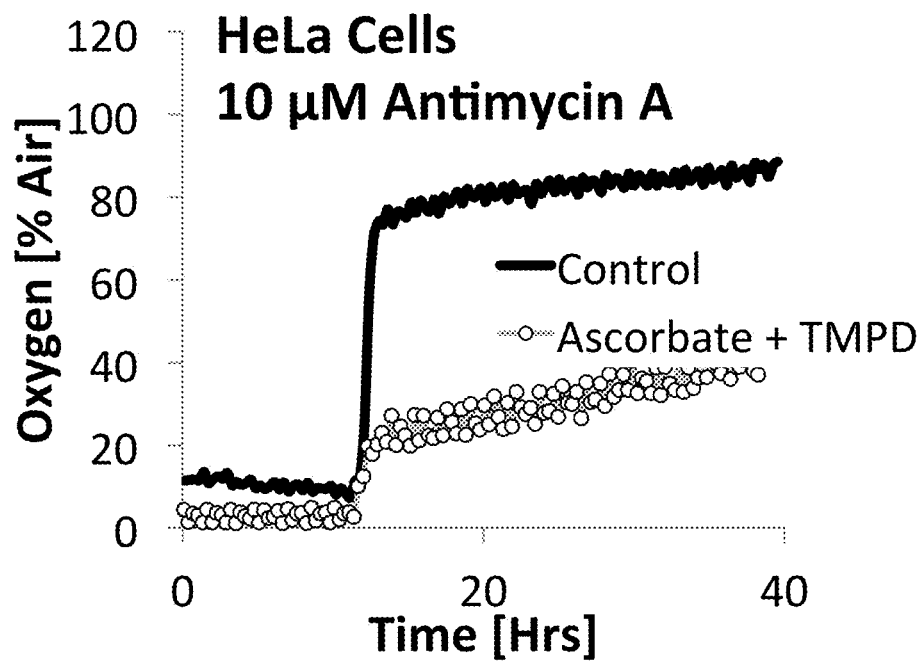

Finally, to confirm the ability of the system and method of the invention to detect damage to mitochondrial complex III, HeLa cells were exposed to 10 μM Antimycin A, a chemical piscicide directly binding cytochrome C (FIG. 4K). Antimycin A showed a similar immediate loss of oxygen uptake that was abrogated by treatment with Ascorbate and TMPD (FIG. 4K).

Figure 4L:
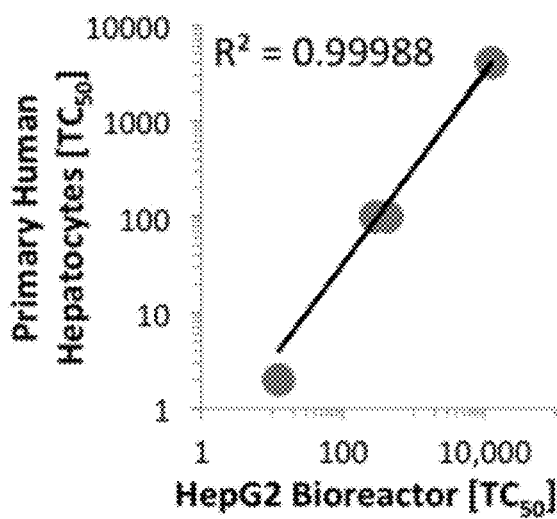

Lastly, comparison of the bioreactor results to primary human hepatocytes (IVIVC) across 4 drugs, including acetaminophen, amiodarone, troglitazone, and rotenone showed an $R^2$ of 0.99 (FIG. 4L).

Example 5

Figure 5A:
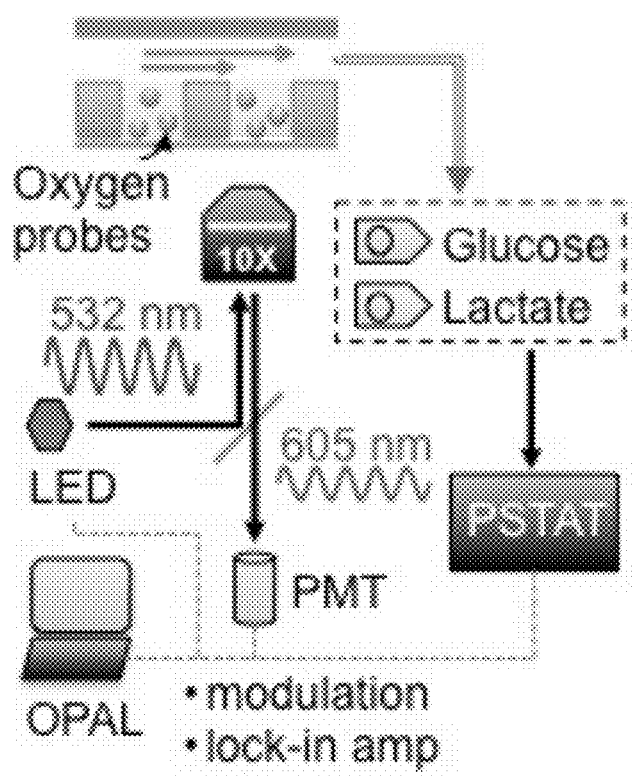
FIGS. 5A-I. 5A: System schematic. 5B: Electrochemical sensor for glucose and lactate based on membrane immobilized glucose oxidase (GOx) and lactate oxidase (LOx). 5C: Microfluidic low-volume PMMA housing for sensors. 5D: Two-layer PDMS microfluidic switchboard with 11 independent computer controlled channels. 5E: Switchboard PDMS micromechanical valves. Flow channel (red); Control channel (blue). 5F: Oxygen uptake, glucose uptake, and lactate production of HepG2/C3A cells exposed to 50 μM rotenone a complex I inhibitor. 5G: Lactate/glucose ratio shows rotenone-induced shift to from mitochondrial respiration to glycolysis followed by glutaminolysis. 5H: Oxygen, glucose uptake, and lactate production of HepG2/C3A cells exposed to 50 μM Troglitazone, an anti-diabetic drug. At this concentration Troglitazone doesn't show any adverse effect. 5I: Lactate/glucose ratio shows Troglitazone-induced gradual shift from mitochondrial respiration toward glycolysis suggesting mitochondrial damage.
Figure 5B:
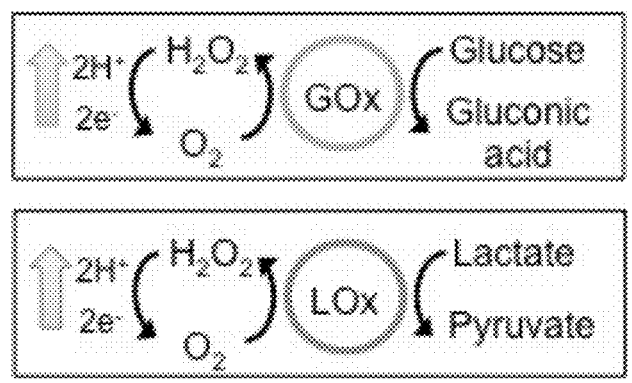
Figure 5C:
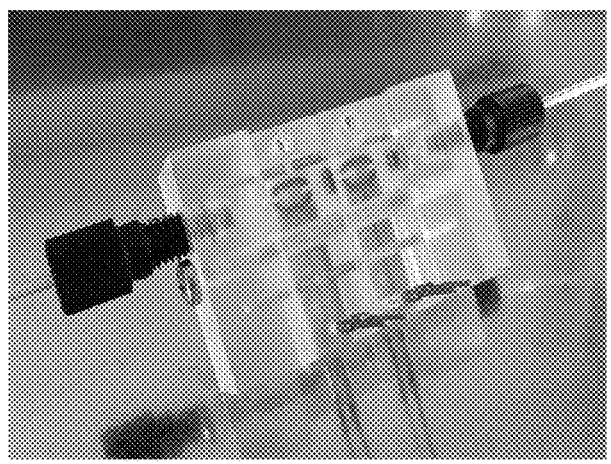
Figure 5D:
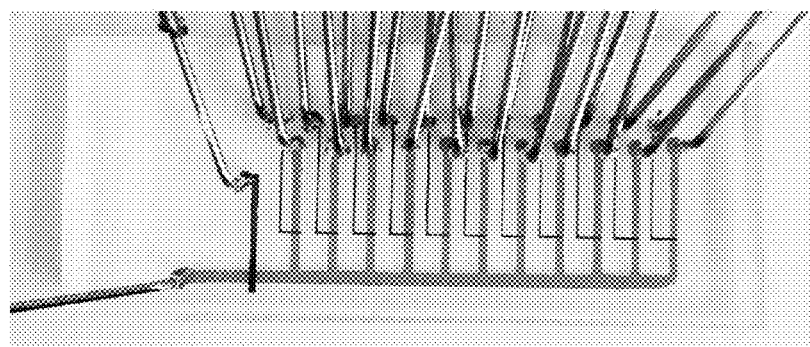
Figure 5E:
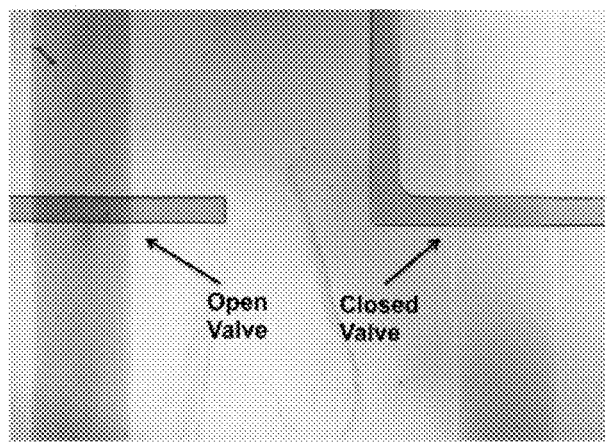
Figure 5F:
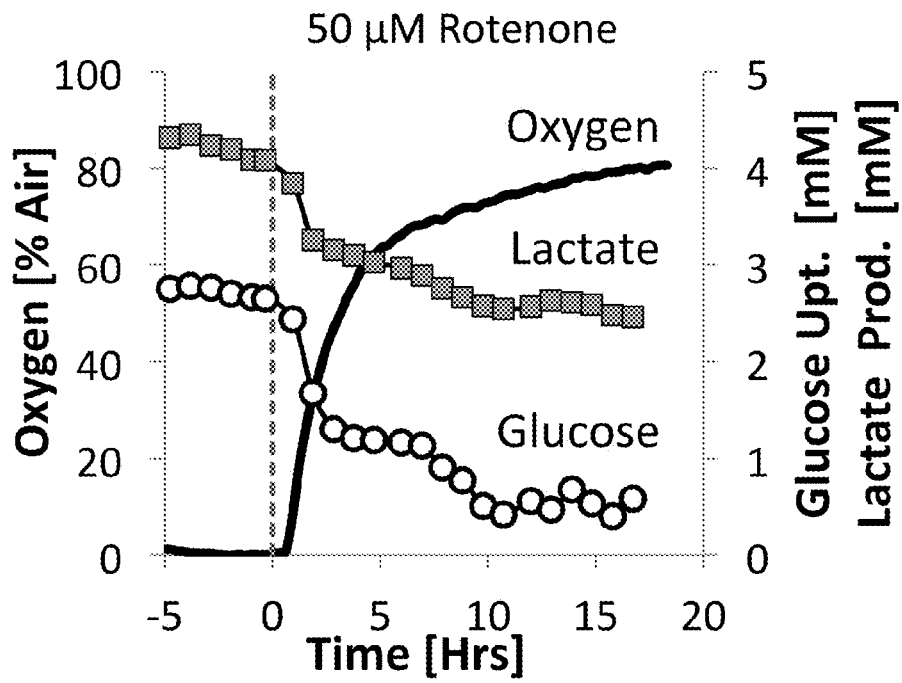
Figure 5G:
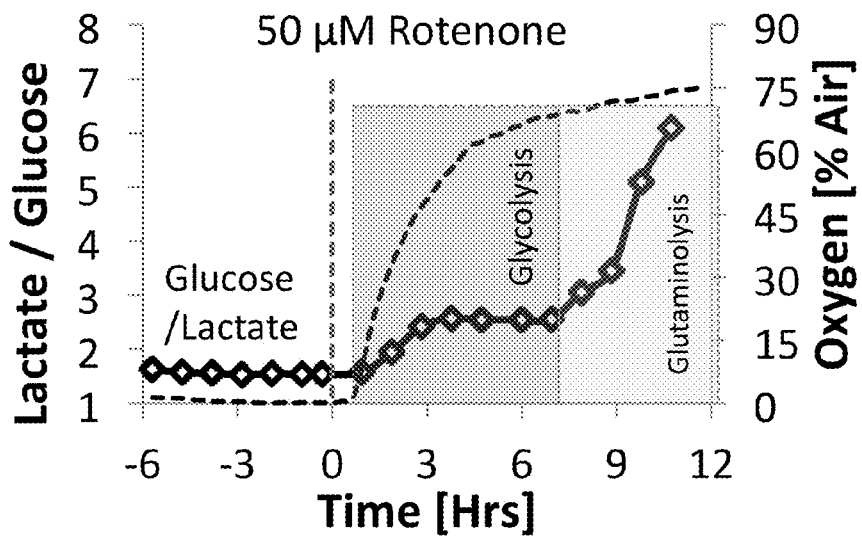
Figure 5H:
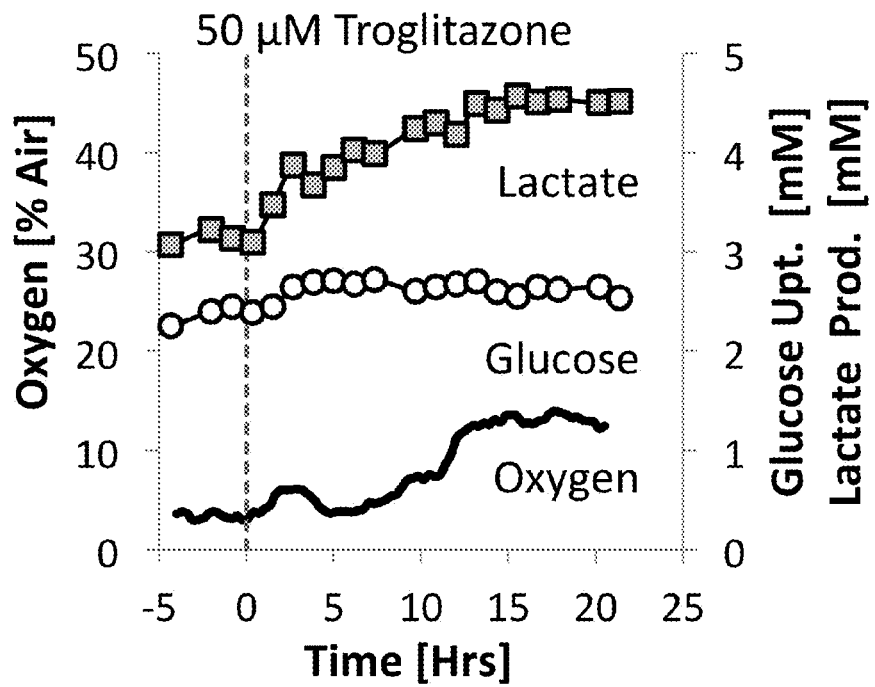
Figure 5I:
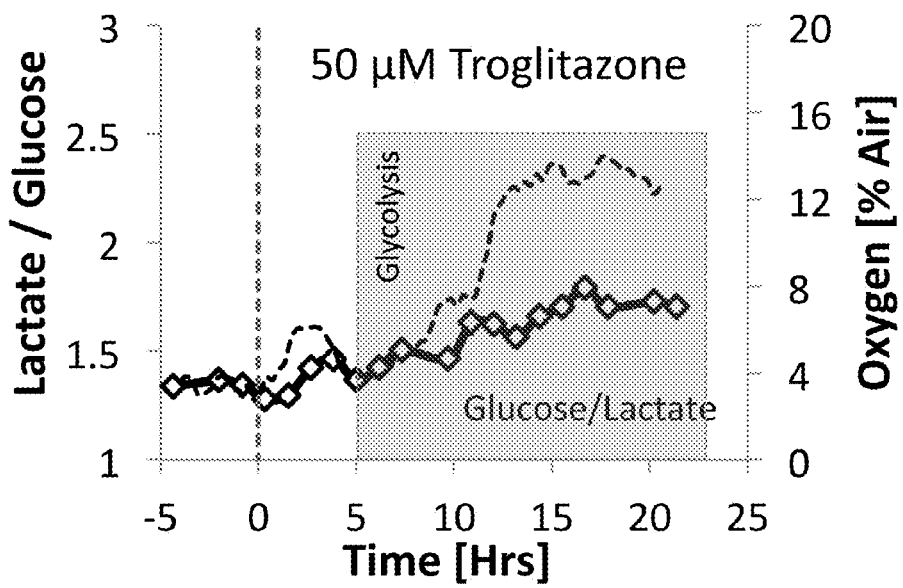

Automated Real-Time Measurement of Circulating Glucose and Lactate Concentrations Cells respond to mitochondrial dysfunction by adapting their metabolic response to circumvent oxidative phosphorylation. To track this response electrochemical sensors for glucose and lactate were attached to bioreactor outflow in a PMMA housing with 16 μl dead volume (FIG. 5 A-C). Samples were collected sequentially using a computer controlled microfluidic switchboard (FIG. 5D). Micromechanical valves (FIG. 5E) introduced a sequence of (1) washing buffer, (2) air bubble interface, and (3) a bioreactor sample every hour. Proof of principle was shown with 50 μM rotenone, a direct mitochondrial C1 inhibitor, causing an 80% loss in respiration (FIG. 5F). Interestingly, lactate is generally produced from glucose at a 2:1 ratio or from glutamine by glutaminolysis. HepG2/C3A cells exposed to rotenone showed a rapid increase in lactate over glucose ratio from 1.3 to 2.5, suggesting a shift toward glycolysis (FIG. 5G). After 6 hours, metabolic collapse was permeated by a shift to glutaminolysis and loss of glucose uptake. Importantly, the system is sensitive enough to detect minute signals and off target effects. For example, exposure to 50 μM Troglitazone, an anti-diabetic drug, causes no adverse effect ($TC_{50}=300$ μM). However, we could detect a minor reduction in oxygen uptake paralleled by a small increase in lactate production, while glucose uptake remained constant (FIG. 5H). Lactate over glucose ratio increases slightly from 1.2 to 1.8, showing a shift toward glycolysis (FIG. 5I).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A perfusion bioreactor system comprising:
    a) a disposable chip comprising one or more micro-wells, each of said one or more micro-wells holding viable cells and forming a tissue;
    b) a connector for connecting the disposable chip to a perfusion element for flowing a perfusion medium in a controlled manner through the disposable chip to provide shear force and nutrient supply; and
    c) one or more oxygen sensing particles embedded in the tissue,
    wherein said micro-wells protect the cells from sheer force.

2. The system according to claim 1, further comprising a glucose sensor and/or a lactate sensor.

3. The system according to claim 2 wherein the lactate and/or glucose sensors are electrochemically operated and/or wherein the glucose and/or lactate sensor are fluorescent or phosphorescent particles.

4. The system according to claim 1, wherein the diameter of each of the micro-well is 75 to 3000 micrometers.

5. The system according to claim 1 wherein the microchip comprises a plurality of micro-channels orthogonal to the direction of flow of the perfusion medium.

6. The system according to claim 1 wherein said oxygen sensing particles are fluorescent or phosphorescent particles.

7. The system according to claim 6, wherein said oxygen sensing particles comprise ruthenium-phenanthroline-based phosphorescence dye.

8. The system according to claim 1, further comprising a measuring unit configured to detect and/or mesure oxygen, glucose and/or lactate by change of at least one of the following parameters: (a) frequency shift, (b) phase shift, or (c) normalized changed in amplitude.

9. The system according to claim 1 wherein the oxygen sensing particles are a priori present on the microchip or wherein the oxygen sensing particles are present in a separate container.

10. The system according to claim 1 wherein the system has a flow inlet for providing medium and a flow outlet for withdrawing medium.

11. The system according to claim 10, wherein the glucose and/or the lactate sensor are present in the flow outlet.

12. The system according to claim 1 wherein the cells are selected from the group consisting of: hepatocytes, cardiomyocytes, kidney cells, neurons, enterocytes, and cell lines mimicking their function.

13. The system according to claim 1 comprising two or more types of cells placed in separate micro-wells or mixed together.

14. The system according to claim 13 wherein the mixed cells are hepatocytes and non-parenchymal cells.

15. A method for testing the effect of a substance of interest on one or more physiological parameters of cells the method comprising:
   a) providing a system, said system comprising:
      a disposable chip comprising one or more micro-wells;
      a connector for connecting the disposable chip to a perfusion element for flowing a perfusion medium in a controlled manner through the disposable chip to provide shear force and nutrient supply;
   b) providing one or more oxygen sensing particles;
   c) introducing cells to the micro-well of said system together with said oxygen sensing particles to form a cellular aggregate within the micro-well having said one or more oxygen sensing particles embedded within said cellular aggregate;
   d) introducing the substance of interest to the chip; and
   e) monitoring changes in oxygen uptake by said cells, thereby testing the effect of a substance of interest on one or more physiological parameters of cells.

16. The method according to claim 15, wherein said oxygen sensing particles are fluorescent or phosphorescent particles.

17. The method according to claim 15, wherein the system comprises a glucose sensor and/or a lactate sensor, the method further comprises monitoring changes in glucose and/or lactate parameters.

18. A method according to claim 15, wherein the substance to be tested is a substance for use in the cosmetic, pharmaceutical, food and/or agriculture industry.

* * * * *